US011872053B1

(12) United States Patent
Ross-Howe et al.

(10) Patent No.: US 11,872,053 B1
(45) Date of Patent: *Jan. 16, 2024

(54) SYSTEMS AND METHODS FOR MONITORING MEDICATION EFFECTIVENESS

(71) Applicant: Cloud Dx, Inc., Brooklyn, NY (US)

(72) Inventors: Sara Ross-Howe, Campbellville (CA); Vesal Badee, Kitchener (CA); Lamiaa Amzil, Cambridge (CA); Robert Kaul, Brooklyn, NY (US)

(73) Assignee: Cloud DX, Inc., Brooklyn, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/190,633

(22) Filed: Mar. 27, 2023

Related U.S. Application Data

(63) Continuation-in-part of application No. 16/673,611, filed on Nov. 4, 2019, now Pat. No. 11,612,352, (Continued)

(51) Int. Cl.
*A61B 5/00* (2006.01)
*A61B 5/0205* (2006.01)
(Continued)

(52) U.S. Cl.
CPC .......... *A61B 5/4848* (2013.01); *A61B 5/0205* (2013.01); *A61B 5/4833* (2013.01); (Continued)

(58) Field of Classification Search
None
See application file for complete search history.

(56) References Cited

U.S. PATENT DOCUMENTS 6,047,203 A * 4/2000 Sackner ............... A61B 5/6805
600/509
6,416,471 B1 * 7/2002 Kumar ................. A61B 5/0022
128/903
(Continued)

FOREIGN PATENT DOCUMENTS

WO  WO2013019188 A1   7/2013

OTHER PUBLICATIONS

Lazazzera et. al., Sensors (Basel). Jun. 4, 2019;19(11):2557.
(Continued)

*Primary Examiner* — Carl H Layno
(74) *Attorney, Agent, or Firm* — Stephen E. Zweig

(57) ABSTRACT

System and method for determining real-world effectiveness of various prescribed medications. Here a variety of different types of patient pulse wave measurements (e.g., blood pressure, pulse oximeter, ECG) and other physiological measurements are obtained. This actual data is compared to calculated measurements that would be expected based on various patient baseline measurements in the absence of medication, schedule of medications, and impact of medications the various patient baseline measurements. If the actual data meets expectations, then the medication is likely acting as anticipated. Depending on which types of data do not meet expectations, problems with one or more previously described medications may be reported. Other types of patient physiological readings, such as temperature, motion, lung function, brain wave function (EEG) and the like may also be obtained, these additional types of readings can be used to extend the range of different types of drugs/medications that the system can successfully monitor.

22 Claims, 6 Drawing Sheets

Related U.S. Application Data which is a continuation-in-part of application No. 16/036,551, filed on Jul. 16, 2018, now Pat. No. 10,893,837, and a continuation-in-part of application No. 15/954,250, filed on Apr. 16, 2018, now Pat. No. 10,463,299, which is a continuation-in-part of application No. 15/060,514, filed on Mar. 3, 2016, now Pat. No. 9,946,844, which is a continuation-in-part of application No. 14/186,151, filed on Feb. 21, 2014, now Pat. No. 10,022,053.

(60) Provisional application No. 62/138,377, filed on Mar. 25, 2015, provisional application No. 61/767,839, filed on Feb. 22, 2013.

(51) Int. Cl.
- *G16H 40/67* (2018.01)
- *A61B 5/024* (2006.01)
- *A61B 5/318* (2021.01)
- *A61B 5/021* (2006.01)
- *A61B 5/145* (2006.01)

(52) U.S. Cl.
CPC ............ *G16H 40/67* (2018.01); *A61B 5/021* (2013.01); *A61B 5/024* (2013.01); *A61B 5/14542* (2013.01); *A61B 5/318* (2021.01)

(56) References Cited

U.S. PATENT DOCUMENTS

| | | | | |
|---|---|---|---|---|
| 7,054,679 B2* | 5/2006 | Hirsh | ............ | A61B 5/029 600/513 |
| 10,463,299 B1* | 11/2019 | Kohli | ............ | A61B 5/0205 |
| 10,893,837 B2* | 1/2021 | Kohli | ............ | G16H 40/63 |
| 2003/0135392 A1* | 7/2003 | Vrijens | ............ | G16H 20/13 705/2 |
| 2003/0156143 A1* | 8/2003 | Westenskow | ............ | G16H 50/50 715/848 |
| 2004/0122484 A1* | 6/2004 | Hatlestad | ............ | G16H 15/00 607/60 |
| 2004/0122486 A1* | 6/2004 | Stahmann | ............ | A61B 5/74 607/60 |
| 2004/0147969 A1* | 7/2004 | Mann | ............ | A61B 5/02108 607/17 |
| 2004/0267321 A1* | 12/2004 | Boileau | ............ | G16H 50/20 607/9 |
| 2005/0137481 A1* | 6/2005 | Sheard | ............ | G16H 40/67 600/508 |
| 2005/0233459 A1* | 10/2005 | Melker | ............ | G01N 33/497 436/56 |
| 2006/0047538 A1* | 3/2006 | Condurso | ............ | G16H 40/67 705/3 |
| 2006/0058917 A1* | 3/2006 | Vonk | ............ | A61J 7/0481 700/236 |
| 2006/0122863 A1* | 6/2006 | Gottesman | ............ | G16H 10/60 705/2 |
| 2006/0122864 A1* | 6/2006 | Gottesman | ............ | G16H 20/17 600/300 |
| 2006/0149330 A1* | 7/2006 | Mann | ............ | A61N 1/37229 607/34 |
| 2006/0224326 A1* | 10/2006 | St. Ores | ............ | G16H 40/67 702/19 |
| 2006/0224421 A1* | 10/2006 | St. Ores | ............ | G16H 10/20 705/4 |
| 2006/0258952 A1* | 11/2006 | Stahmann | ............ | A61B 5/4878 600/528 |
| 2007/0021979 A1* | 1/2007 | Cosentino | ............ | A61B 5/0031 600/300 |
| 2007/0073590 A1* | 3/2007 | Cosentino | ............ | G01G 23/3735 705/22 |
| 2007/0156626 A1* | 7/2007 | Roehm | ............ | G16Z 99/00 706/924 |
| 2007/0208263 A1* | 9/2007 | John | ............ | A61B 5/349 600/509 |
| 2007/0287923 A1* | 12/2007 | Adkins | ............ | A61B 5/022 600/485 |
| 2008/0051767 A1* | 2/2008 | Rossing | ............ | A61M 5/1723 604/502 |
| 2008/0154098 A1* | 6/2008 | Morris | ............ | A61B 5/002 600/300 |
| 2009/0024176 A1* | 1/2009 | Yun | ............ | A61N 1/3627 607/20 |
| 2009/0058635 A1* | 3/2009 | LaLonde | ............ | A61B 5/349 340/539.11 |
| 2009/0062671 A1* | 3/2009 | Brockway | ............ | A61B 5/361 600/518 |
| 2009/0299156 A1* | 12/2009 | Simpson | ............ | A61B 5/0002 600/301 |
| 2011/0009715 A1* | 1/2011 | O' Reilly | ............ | G16H 20/30 600/302 |
| 2011/0112860 A1* | 5/2011 | Kehr | ............ | G16H 20/10 705/2 |
| 2011/0151418 A1* | 6/2011 | Delespaul | ............ | G16H 20/70 434/236 |
| 2011/0172504 A1* | 7/2011 | Wegerich | ............ | A61B 5/7264 600/301 |
| 2011/0179159 A1* | 7/2011 | Eglington | ............ | G08B 21/0423 709/224 |
| 2011/0224912 A1* | 9/2011 | Bhavaraju | ............ | A61B 5/4848 702/19 |
| 2011/0245633 A1* | 10/2011 | Goldberg | ............ | A61B 5/165 600/323 |
| 2012/0086573 A1* | 4/2012 | Bischoff | ............ | G08B 21/0492 340/573.1 |
| 2012/0203573 A1* | 8/2012 | Mayer | ............ | G16H 40/63 705/3 |
| 2012/0323592 A1* | 12/2012 | Bechtel | ............ | G16Z 99/00 705/2 |
| 2013/0184599 A1* | 7/2013 | Friedman | ............ | A61B 5/1477 600/509 |
| 2013/0296823 A1* | 11/2013 | Melker | ............ | A61M 5/16854 604/503 |
| 2014/0107493 A1* | 4/2014 | Yuen | ............ | A61B 5/7455 600/479 |
| 2014/0236025 A1* | 8/2014 | Sheldon | ............ | A61B 5/0205 600/483 |
| 2015/0112606 A1* | 4/2015 | He | ............ | A61B 5/02055 702/19 |
| 2015/0164351 A1* | 6/2015 | He | ............ | A61B 5/0285 702/19 |
| 2016/0188839 A1* | 6/2016 | Kaul | ............ | G16H 40/67 705/2 |
| 2016/0256060 A1* | 9/2016 | Katra | ............ | A61N 1/395 |
| 2016/0302666 A1* | 10/2016 | Shaya | ............ | G16H 40/67 |
| 2016/0302677 A1* | 10/2016 | He | ............ | A61B 5/1102 |
| 2016/0371462 A1* | 12/2016 | Wallen | ............ | A61J 1/035 |
| 2017/0124276 A1* | 5/2017 | Tee | ............ | G08B 21/0446 |
| 2017/0238812 A1* | 8/2017 | Atlas | ............ | A61B 5/1117 |
| 2017/0246086 A1* | 8/2017 | Jain | ............ | A61J 7/0481 |
| 2018/0158551 A1* | 6/2018 | Bradley | ............ | H04L 63/0861 |

OTHER PUBLICATIONS

Xing et al., Sci Rep 9, 8611 (2019).
Haddad et. al., IEEE J Biomed Health Inform. May 2022;26(5):2096-2105.
Carlson et. al., Sensors. 2021; 21(1):156.
He et al., Annu Int Conf IEEE Eng Med Biol Soc. 2012;2012:5030-3.
Kim et. al., IEEE Trans. Biomed. Eng. 2018, 65, 2384-2391.
Foo et. al., Physiol. Meas. 27, 685 (2006).
Chen et. al., Med. Biol. Eng. Comput., vol. 38, No. 5, pp. 569-574, Sep. 2000.
Poon et. al., Proc. 27th Annu. Int. Conf. IEEE Eng. Med. Biol. Soc., Shanghai, China, 2006, pp. 5877-5880.
Verkruysse et. al., Opt Express. (2008) 16:21434-45.
Jeong et. al., J Med Syst. (2016) 40:77.

(56) References Cited

OTHER PUBLICATIONS

Jain et. al., Conference Proceedings: 2016 IEEE 18th International Workshop on Multimedia Signal Processing (MMSP). (2016) 1-5.
Alizadeh, Remote Monitoring of Human Vital Signs Using mm-Wave FMCW Radar. IEEE Access. pp. 1-1. 10.1109/ACCESS.2019.2912956.
Wang et. al., Remote Monitoring of Human Vital Signs Based on 77-GHz mm-Wave FMCW Radar. Sensors. 2020; 20 (10):2999.
Omer et. al., (2018) Non-invasive Glucose Monitoring at mm-Wave Frequencies. Journal of Computational Vision and Imaging Systems. 4. 3. 10.15353.
N.S. Altman, "An Introduction to Kernel and Nearest-Neighbor Nonparametric Regression", The American Statistician 46(3), 1992, pp. 175-185).
Ganesan et. al., "Application of Neural Networks in Diagnosing Cancer Disease Using Demographic Data", International Journal of Computer Applications (0975-8887) vol. 1—No. 26, 2010.
Cortes and Vapnick, "Support-vector networks", Machine Learning Sep. 1995, vol. 20, Issue 3, pp. 273-297.

\* cited by examiner

SYSTEMS AND METHODS FOR MONITORING MEDICATION EFFECTIVENESS

CROSS REFERENCE TO RELATED APPLICATIONS

This application is a continuation in part of U.S. patent application Ser. No. 16/673,611, filed Nov. 4, 2019, now U.S. Pat. No. 11,612,352 issued Mar. 28, 2023; application Ser. No. 16/673,611 was a continuation in part of U.S. patent application Ser. No. 15/954,250, filed Apr. 16, 2018, now U.S. Pat. No. 10,463,299 issued Nov. 5, 2019; application Ser. No. 15/954,250 was a continuation in part of U.S. patent application Ser. No. 15/060,514, filed Mar. 3, 2016, now U.S. Pat. No. 9,946,844 issued Apr. 17, 2018; application Ser. No. 15/060,514 claimed the priority benefit of U.S. provisional application 62/138,377, "COMPREHENSIVE BODY VITAL SIGN MONITORING SYSTEM WITH NECK AND EAR MOUNTED DEVICE, filed Mar. 25, 2015; application Ser. No. 15/060,514 was also a continuation in part of U.S. patent application Ser. No. 14/186,151 "SIMULTANEOUS MULTI-PARAMETER PHYSIOLOGICAL MONITORING DEVICE WITH LOCAL AND REMOTE ANALYTICAL CAPABILITY", filed Feb. 21, 2014, now U.S. Pat. No. 10,022,053 issued Jul. 17, 2018; application Ser. No. 14/186,151 in turn claimed the priority benefit of U.S. provisional application 61/767,839 "SIMULTANEOUS MULTI-PARAMETER PHYSIOLOGICAL MONITORING DEVICE WITH DUAL LOCAL AND REMOTE ANALYTICAL CAPABILITY", filed Feb. 22, 2013; application Ser. No. 16,673,611 was also a continuation in part of U.S. patent application Ser. No. 16/036,551, filed Jul. 16, 2019, now U.S. Pat. No. 10,893,837, issued Jan. 19, 2021; the entire contents of all of these applications are incorporated herein by reference in their entirety.

BACKGROUND OF THE INVENTION

Field of the Invention

This invention is in the field of patient operated medical diagnostic devices that can be used to determine if a patient is being effectively treated by health care provider medication prescriptions.

Description of the Related Art

Although patients are often prescribed multiple medications, the effectiveness of such prescriptions is often suboptimal. Such ineffectiveness can be due to different causes, such as patient non-adherence to the prescriptions (e.g., not taking the prescribed drugs properly), or alternatively, because the patient's body is not reacting to the drug (or drug combination) as expected or as desired (e.g., adverse drug interactions, and the like). In this later situation, the patient's body may have originally reacted as expected, but then, due to various other factors, may with time or disease progression, or unexpected interaction with other drugs may no longer be reacting with the drug as the patient's body did originally. Patient non-adherence to health care provider mediation recommendations is a major medical problem. Center for Disease Control (CDC) materials suggest that between 20-30% of medication prescriptions are never filled, and medication is not taken as prescribed in up to 50% of all cases.

For example, studies have shown that only about 51% of patients being treated for hypertension are adherent to their medication therapy on a long term basis. In this context, "long term" should be viewed as being about six months, since other studies have shown that medication adherence rates drop off after the first six months of treatment. This is a large-scale problem. At present over 133 million Americans have a long term chronic condition requiring medication.

It has also been estimated that medication non-adherence can result in up to 125,000 excess deaths annually; also incurring economic costs (due to higher subsequent patient expenses) estimated at $100 billion to $300 billion dollars per year.

Thus, methods to monitor and encourage patent adherence to prescribed medications are of high interest in the art. Patient adherence to hypertension medication is particularly critical.

Patients, in particular elderly patients, are often put on multiple different medications at the same time. For example, to control hypertension, patients may be put on various combinations of diuretics, angiotensin converting enzyme (ACE) inhibitors, angiotensin receptor blockers (ARBs), beta-blockers, vasodilators, calcium channel blockers, aldosterone antagonists, renin inhibitors, alpha blockers, and the like. No one drug alone may be totally effective, but in combination, several drugs may produce the desired results.

Patients with other types of disorders, such as lung disease, chronic obstructive pulmonary disease, epilepsy, diabetes, and the like are of course not immune to hypertension. Many of these patients, sometimes in addition to anti-hypertension drugs, also take additional types of drugs for these disorders. It is not uncommon for these other drugs to also have an impact on cardiovascular system function as well.

In order to improve patient medication adherence, the patient should ideally receive frequent feedback that would promptly warn the patient whenever the patient is not adhering to their prescribed medication properly, or when this medication has otherwise become less than fully effective.

A few such patient operated medical diagnostic tests are presently on the market, such as home blood glucose tests, home blood pressure tests, home pulse oximeters, and even home ECG tests.

With the exception of home tests for blood glucose, there are presently few home diagnostic tests that can warn a patient when he or she is out of compliance for a particular medication. Here prior art home blood pressure tests illustrate the problem—if a patient's blood pressure is non-ideal, is this because the patient skipped one of several anti-hypertensive medications that the patient has been taking, or is it simply because the patient is having a bad day? If the patient skipped a drug, which one was skipped?

Thus, further improvements in the art of using patient operated medical diagnostics to monitor patient adherence to medication would be desirable.

Blood Pressure Monitoring Technology:

Although automated oscillometric cuff type methods of obtaining blood pressure and pulse wave profiles are highly popular in the art, other non-cuff methods are also known. These include photoplethysmography, ballistocardiography, phonocardiography, advanced electrocardiography techniques, video analysis, and radar methods.

Photoplethysmography methods are taught by the work of Lazazzera et. al., Sensors (Basel). 2019 Jun. 4; 19(11):2557;

Xing et. al., Sci Rep 9, 8611 (2019); Brophy et. al. Sensors. 2021; 21(18):6311; and Haddad et. al., IEEE J Biomed Health Inform. 2022 May; 26(5):2096-2105.

Ballistocardiography methods are taught by the work of Carlson et. al., Sensors. 2021; 21(1):156; He et. al., Annu Int Conf IEEE Eng Med Biol Soc. 2012; 2012:5030-3; Kim et. al., IEEE Trans. Biomed. Eng. 2018, 65, 2384-2391; Su et. al., IEEE Trans. Biomed. Eng. 2019, 66, 740-748, and Chen et. al., US20150018637A1 (2015).

Phonocardiography methods are taught by the work of Foo et. al, Physiol. Meas. 27, 685 (2006).

Advanced Electrocardiography methods are taught by the work of Chen et. al., Med. Biol. Eng. Comput., vol. 38, no. 5, pp. 569-574, September 2000; and Poon et. al., Proc. 27th Annu. Int. Conf. IEEE Eng. Med. Biol. Soc., Shanghai, China, 2006, pp. 5877-5880.

Video analysis methods are taught by the work of Verkruysse et. al., Opt Express. (2008) 16:21434-45; Jeong et. al., J Med Syst. (2016) 40:77; and Jain et. al., Conference Proceedings: 2016 IEEE 18th International Workshop on Multimedia Signal Processing (MMSP). (2016) 1-5.

Radar based methods includes the work of Alizadeh, Remote Monitoring of Human Vital Signs Using mm-Wave FMCW Radar. IEEE Access. PP. 1-1. 10.1109/ACCESS.2019.2912956; Wang et. al., Remote Monitoring of Human Vital Signs Based on 77-GHz mm-Wave FMCW Radar. Sensors. 2020; 20(10):2999; and Omer et. al., (2018) Non-invasive Glucose Monitoring at mm-Wave Frequencies. Journal of Computational Vision and Imaging Systems. 4. 3. 10.15353.

BRIEF SUMMARY OF THE INVENTION

The invention is based, in part, on the insight that various types of patient operated instrumentation, such as blood pressure monitors, pulse oximeters, ECG readers and the like discard a huge amount of data in the course of obtaining their various different types of pulse wave measurements and other types of measurements. This invention is also based, in part, on the insight that with proper analysis, this massive amount of blood pressure data, pulse oximeter data, ECG reading data, and other types of data could be usefully employed to help solve the major problem of monitoring issues of patient medication adherence and medication effectiveness. In some embodiments, the invention may be a method, device or system for determining any of an efficacy of a medication regimen, and any of the effectiveness of, or a patient's adherence to, a prescribed medication regimen. The invention relies on a plurality of different types of measured (actual) patient pulse wave measurements, such as some combination of oscillometric blood pressure data, oscillometric pulse oximeter data, and ECG data, as well as other types of patient physiological measurements as available.

In this context, medication effectiveness represents the total impact of the various medications that the patient is actually taking on the patient's physiology (e.g., medical status), as compared to what the prescribing physician(s) (or other healthcare workers) may have intended based on the patient's medication regimen. The actual medication effectiveness may differ from what the prescribing physician intended due to multiple factors, including lack of patient medication adherence (e.g., the patient just is not taking the pills properly), adverse drug interactions, changes in patient medical status, unexpected side effects, and the like. Here the term "determining an effectiveness" is intended to communicate that the invention is configured to report or "sound an alarm" when any of these problems are detected. This alerts the patient and healthcare to the fact that there is an unexpected mediation problem, and that further investigation as to the underlying cause of the problem may be needed.

As an analogy, consider a smoke detector versus a combined carbon monoxide and smoke detector. "Determining patient adherence" is somewhat like a fire detector, while "determining an effectiveness" is somewhat like a combined smoke detector and carbon monoxide detector. Although lack of "effectiveness" is a more general problem than lack of "adherence", and may require more follow up investigation to determine if the lack of effectiveness was caused by lack of adherence, adverse drug interactions, changes in patient medical status, or unexpected side effects, nonetheless determining (medication) effectiveness can sometimes be even more valuable than determining patient adherence because it can find more problems.

The invention further relies on additional information, such as patient reference (baseline) information that reports on the various patient pulse wave measurements in the absence of various types of medication, medication schedule information (which informs the invention as to what types of drugs/medications that patient should be taking, and when), and medication impact parameters, which informs the invention as to how the various individual medications would be expected to impact (alter) various specific types of patient pulse wave measurements. Additional information, such as blood glucose sensor data from blood glucose meters, patient motion data from handheld computerized devices such as smartphones, skin electrical conductance sensors (e.g., galvanic skin detectors, also called GSR), sound analysis, and patient interview data can also be used by the invention.

The invention will typically use at least one processor to obtain various different types of actual patient pulse wave measurements and optionally other types of data as well. It will then use its various types of additional information to determine if the actual data is as expected based on the patient baseline pulse wave information, expected medication schedule, and expected impact of these medications on the patient baseline pulse wave information. If the results are inconsistent, then the invention will typically conclude that the patient is not responding as expected and that either the patient is not properly adhering to his medication schedule, or that the medication is not acting as expected/desired, and will report these problems accordingly.

Other types of patient physiological readings, such as temperature, motion, lung function (e.g. stethoscope-like microphone pickups and automated sound analysis, spirometers, actual or computed respiration rate data), brain wave function (EEG), imported blood glucose data from blood glucose sensors, motion data from accelerometers or motion sensors on handheld portable computerized devices such as smartphones, and the like may also be obtained, and these additional types of readings can be used to extend the range of different types of drugs/medications that the system can successfully monitor.

Note that in some embodiments, "effectiveness" may be defined as an impact of at least one specific medication on a patient's actual patient pulse wave measurements as compared to calculated expected patient pulse wave measurements for this medication regimen.

DETAILED DESCRIPTION OF THE INVENTION

Figure 1:
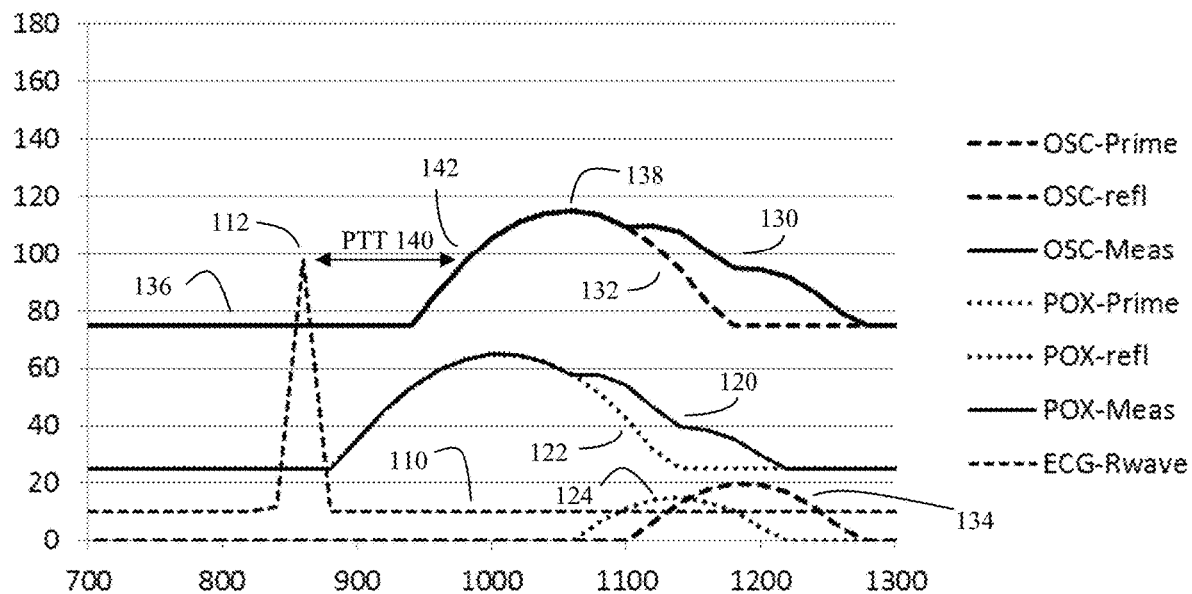
FIG. 1 shows a simplified drawing of patient reference pulse wave measurements for a normal (healthy patient) in the absence of medication. Three different types of patient pulse wave measurements (oscillometric blood pressure measurements, pulse oximeter type measurements, and ECG measurements) are being shown simultaneously, along with some of the underlying patient physiological mechanisms that create some of these various patient pulse waves. Here the time elapsed from the last previous ECG "R" pulse (in milliseconds) is shown on the "X" (horizontal) axis. The "Y" vertical axis shows (for the blood pressure measurements) the blood pressure in millimeters of mercury (mm Hg), or arbitrary units for the other pulse wave measurements.

Medication (drug) effectiveness is defined by the Merck Manual as "how well a drug works in real-world use". This definition of effectiveness takes into account the fact that essentially all drugs have a risk/benefit ratio, and that drugs frequently have side-effects, or undesired interaction with other medications (other drugs), that might limit their use in the real-world.

Thus, while a drug might appear to work well in clinical trials when studied by itself, in the real-world, where drugs can have undesired side effects, and undesired interactions with other drugs, the performance a drug that might appear to work well in a clinical study where patients are highly monitored and are just taking one drug, might perform quite differently in the real world. In the real world, particularly for elderly patients, the situation is much more complicated. Patients, such as elderly patients, typically are prescribed multiple drugs at the same time. In the real world, these drugs may interact with each other in unexpected ways. Further, as the patient ages, the function of various organs, such as the kidneys (which clear drugs from the patient's body), can deteriorate. Another complication is that patients may occasionally forget to take one or more of their medications, or skip one or more of their medications if that medication is particularly expensive, and/or if the patient comes to believe that a given medication causes undesirable side effects. The net result is that when patients use a plurality of (e.g., multiple) drugs) in real-world situations, many variables come into play, and more sophisticated methods to analyze these situations are desirable.

In addition to prescribed drugs, other substances, such as commonly used foods, drinks, and nutritional supplements that a patient may ingest may also impact the patient's physiology, resulting in unexpected results depending on that patient's medical status and medication schedule.

For example, grapefruit or grapefruit juice interacts with the patient's drug-metabolizing enzymes (such as CYP3A4) in the patient's liver and can cause various drugs to build up to toxic levels, or otherwise interact start to produce unexpected medication results. These unexpected results can show up as various patient physiological changes, such as abnormal heart rhythms, low blood pressure, and difficulty breathing, which can be detected by the various methods of pulse wave analysis described herein.

Unexpected changes in a patient's alcohol consumption, as well as unexpected interactions with certain nutritional supplements, can also result in unexpected changes to a patient's physiology that can be potentially detected by the various described herein.

Chronopharmacology: In addition to the impact of changing patient physiology as the patient's health status changes, and the impact of various foods and nutritional supplements on the patient, other real-world effects include medication timing (e.g., chronopharmacological effects). Human physiology varies according to the patient's circadian rhythms (circadian clock). For example, a patient's ability to absorb drugs through the patient's gastric system will differ according to time of day. A patient's liver may metabolize different drugs differently according to time of day. Further, a patient's kidney function (the kidneys often excrete drugs from the patient's body) can also differ according to time of day. As a result, the function of certain drugs, such as anti-asthma drugs (e.g., theophylline), which impacts breathing and associated pulse wave detectable parameters, can vary according to time of day. The impact of certain antihypertensive (drug pressure) medications, which can impact both patient blood pressure and pulse rates, can also be significantly impacted by the time of day that a patient takes the drugs.

Thus, as a result of these real-world effects, even a patient that might look completely compliant on paper (e.g. always takes their prescribed drugs once a day according to a written prescription) may experience significant changes in real-world medication results due to changes in the time of day the patient takes the drugs, changes in the patient's physiology (even those merely due to a normal aging process, let alone those caused by various diseases), and interactions with various foods and nutritional supplements. In some embodiments, the invention can serve as an "early warning" system to alert the patient and/or the medical practitioner that, for whatever reason, the patient's medication regimen is not working as well "in the real world" as expected.

In this disclosure, the term "real-world effectiveness" is defined as being the effectiveness of a drug, outside of well control trials, when used by non-clinical trial patients, under non-clinical trial conditions, who are subject to the various effects (drug-drug interactions, drug-food interactions, drug-nutraceutical interactions, variations in patient physiology caused by any of aging, genetics, or disease, variations in patient medication adherence, and chronopharmacology effects caused by the time of day, or variations in the time of day, that a patient takes their various drugs) described above.

As one example of how the invention can operate, consider the problem of hypertension. Hypertension is a very common and very serious disease that is frequently treated by multiple anti-hypertensive drugs simultaneously. Often these different types of anti-hypertensive drugs (medications) have different, and sometimes even well understood, mechanisms of action on the user's cardiovascular system.

In this discussion, we will first examine some of the various types of cardiovascular system related pulse wave data that may be obtained by patient operable instrumentation, such as the easy to use multiple sensor instrumentation discussed in more detail in U.S. patent application Ser. No. 14/186,151 and 62/138,377, and shown in FIGS. 8 and 9. In these examples, we will examine some hypothetical automated oscillometric cuff type blood pressure pulse wave profiles, automated oscillometric pulse oximeter type pulse wave profiles, and automated electrocardiogram (ECG) pulse wave profiles, as well as some of the underlying physiological changes brought about by hypertension and various drugs on these pulse wave profiles. These examples are intended to make the general principles behind the invention easier to understand, but are otherwise not intended to be limiting.

In this discussion, automated blood pressure sensors, such as oscillometric cuff type blood pressure sensors will be commonly abbreviated as "oscillometric" or "OSC" sensors regardless of if these sensors actually use cuffs or not. That is for simplicity, other types of blood pressure sensors will also be given this "OSC" label as well. These other types of blood pressure sensors will be discussed in more detail shortly.

Figure 9:
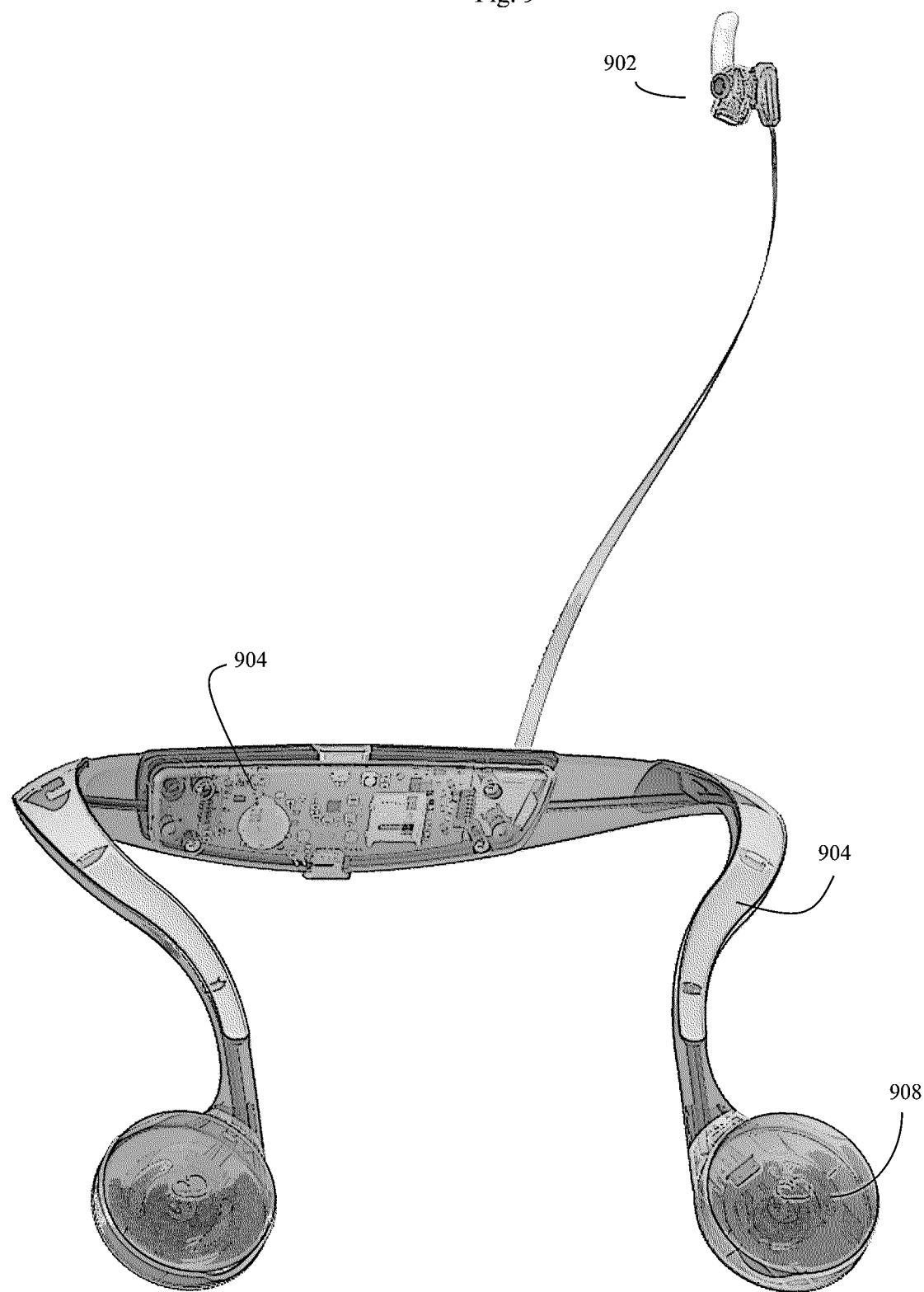
FIG. 9 shows an example of a different type of patient operable instrumentation that, with upgrades as described herein, may be used according to the present invention. In this embodiment, the patient operable instrumentation is intended to be worn by the patient over a period of time.

The automated pulse oximeter type sensors will be commonly abbreviated as "pulse oximeter" or "POX" type sensors, and automated electrocardiogram sensors will be commonly abbreviated as "ECG" sensors. See application Ser. No. 14/186,151 and 62/138,377 for further discussion. Note that although in some embodiments, these three devices (blood pressure sensors, automated pulse oximeter type sensors, and automated electrocardiogram sensors) will all be part of the same unitized device, such as the same patient operable instrumentation, in other embodiments, one or more of these devices may be separate, and instead communicate with the patient operable instrumentation via a wired or wireless channel. For example, a unitized device such as shown in FIG. 9, but lacking an automated oscillometric cuff type blood pressure sensor, might implement the invention by communicating with a separate oscillometric cuff type blood pressure sensor by any of a wired or wireless (e.g., Bluetooth) connection, or by using a non-cuff-based blood pressure sensor. For example, a processor from a device such as FIG. 9 might send commands to, and receive data from, a separate automated oscillometric cuff type blood pressure sensor or non-cuff blood pressure sensor via a Bluetooth or other type link.

FIGS. 1-6 are based on a simplified model of the cardiovascular system. These figures show both the actual measurements that may be obtained by the various pulse wave sensors, as well as a few details of some of the underlying physiological mechanisms that produce these actual measurements.

In these simplified examples, assume that the major components of the patient's systolic blood pressure caused by a combination of the patient's primary pulse pressure (caused by contraction of the patient's left ventricle), augmented by a reflected wave produced when the primary pulse pressure wave effectively "bounces" off of the patient's major arteries. In younger or healthier patients, these arteries are more elastic, and this tends to delay the timing of the return "bounce" or "reflected" pressure wave so that it does not significantly augment the pressure of the primary pulse pressure wave. However, in older or less healthy patients, the arteries are less elastic, and this tends to speed up the timing of the return "bounce" reflected pressure wave so that the reflected wave pressure and the primary wave pressure additively superimpose and augment each other, thus producing a higher (and typically unhealthy) diastolic pressure.

FIG. 1 shows a simplified drawing of patient reference pulse wave measurements for a normal (healthy patient) in the absence of medication. Here the instrumentation is providing three types of "actual" patient "baseline" pulse wave measurements. These types include pulse waves from an electrocardiograph (ECG) type sensor (110), pulse waves obtained from an oscillometric pulse oximeter type sensor (POX) (120), and pulse waves obtained from a blood pressure monitor, such as an oscillometric cuff type blood pressure monitor type sensor or other type blood pressure sensor (OSC) (130).

The actually measured oscillometric type blood pressure waveforms are shown by the solid "OSC-Meas" line (130). These actually measured waveforms are produced by the combination of a primary pulse pressure wave "OSC-Prime" shown in dashed lines (132), and a reflected pulse pressure wave "OSC-refl" shown by the dashed line (134). For these "OSC" waveforms, the vertical "Y" axis should be assumed to read in millimeters of mercury (mm Hg).

The actually measured pulse oximeter blood pressure waveforms are shown by the solid "POX-Meas" line (120). These actually measured waveforms are also produced by the combination of a primary pressure wave "POX-Prime" shown in dotted lines (122) and a reflected pulse pressure wave "POX-refl" (124). Although these measurements could also be expressed in mm Hg, for better readability, the Y axis pulse oximeter readings are shown as being offset from the oscillometric blood pressure readings. Note that the timing and the shape of the pulse oximeter waveforms are not quite the same as the oscillometric type waveforms. This is because the pulse oximeter sensor will typically be located in a different part of the patient's body (e.g., ear lobe, fingertip) than the oscillometric blood pressure sensor (arm, wrist), and the pulse wave will thus take differing amounts of time to reach the two sensors, with the time being controlled by the pulse wave velocity (PWV). Here assume that in this case, the patient's pulse oximeter is mounted on an ear lobe, while the oscillometric blood pressure sensor is mounted on a wrist, and the signal pulse wave reaches the ear lobe first.

In this simplified model, assume that the horizontal "X" axis represents the time (in milliseconds) since the peak of the last ECG "R" wave, which occurs at the same frequency as the patient's pulse. Assume also that the pulse transit time "PTT" (140) is the time delay between the peak of the ECG "R" wave (112) and the rise in the measured pulse (142).

Here also, assume that the baseline of the measured oscillometric waveform (OSC-Meas) (136) represents the patient's diastolic blood pressure, while the peak of the measured oscillometric waveform (138) represents the patient's systolic blood pressure. These same conventions and numbering scheme are used throughout FIGS. 1-6.

In FIG. 1, this ideal normal patient has ideal cardiac parameters, such as a pulse rate of 70 beats per minute, and a blood pressure of 115/75 mm/Hg. When the patient's heart beats (here shown triggered by the ECG "R" wave 112), the contraction of the patient's ventricle produces both a primary wave (OSC-Prime 132) and (due to rebound from the patient's arteries), a time-delayed reflected wave (OSC-refl 134) that, depending on the timing of the reflected wave, can augment or not augment the systolic blood pressure (138) caused by the primary wave.

In this example, assume that the patient has young and flexible arteries. As a result, the reflected wave (134) bounces more slowly, and is thus sufficiently delayed so that the peak pressure of the reflected wave (134) does not add to the peak pressure of the primary wave (132), thus helping to keep the peak systolic pressure (138) at the desired level. Additionally, due to the patient's more flexible arteries, the speed of the pulse transit time (140) (e.g., time between the peak ECG "R" wave (112) and the raising part of the pulse wave 142) also tend to be somewhat longer, and the patient's diastolic blood pressure (136) is also at a lower level.

In this example, the processed pulse oximeter readings (120), (122), (124) are generally similar to the oscillometric cuff type blood pressure readings or other type of blood pressure sensor readings, but due to differences in the location of the two types of sensing device, differ somewhat in timing and pulse shape. Thus to summarize, in FIG. 1, the patient has a normal pulse rate of 70 beats per minute (this can be seen by the fact that the ECG "R" wave (112) has a peak at 857 milliseconds), the patient has a systolic blood pressure reading (138) of 115 mm Hg, a diastolic blood pressure reading (136) of 70 mm Hg, the reflected wave (134) arrives 130 milliseconds after the primary wave (138), and the patent has a pulse transition time (PPT, 140) of 200 milliseconds.

Figure 2:
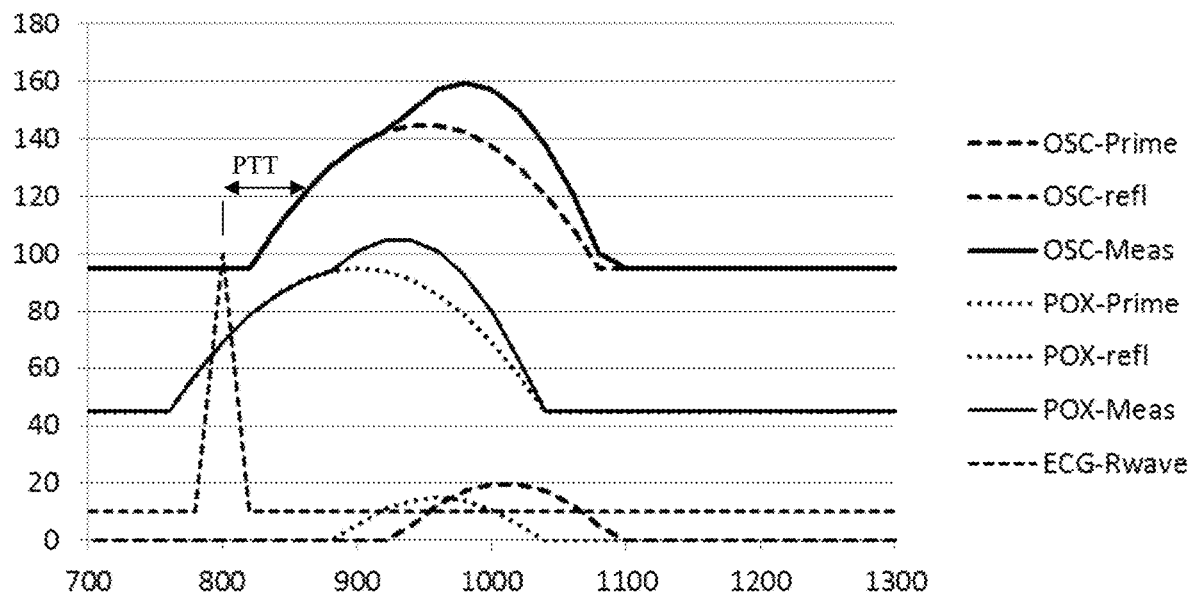
FIG. 2 shows a simplified version the reference pulse wave measurements for a different (older patient suffering from hypertension) patient in the absence of medication. This is this patient's "baseline" pulse wave information. Note the overall higher blood pressure, and different timing of various components of the various pulse waves, relative to FIG. 1.

FIG. 2 shows a simplified version of the same type of patient reference information, but in this case, obtained from an older patient suffering from hypertension. In the absence of any drugs, this older hypertension patient has a somewhat higher pulse rate (75 beats per minute) (note that the ECG "R" wave now is at 800 milliseconds), a higher diastolic blood pressure (136) of about 95 mm Hg because this patient has generally stiffer arteries. Additionally, this patient's coronary arteries are also stiffer, thus, unfortunately, producing a faster acting reflected wave (134) arriving only 60 milliseconds after the primary wave (138). Due to this faster arrival time, the peak of the reflected wave (134) acts to augment the systolic blood pressure produced by the peak of the patient's primary wave (132), producing a high peak systolic blood pressure of 160 over 95 (138). Additionally, the pulse transit time (140) (e.g., time between the peak ECG "R" wave (112) and the raising part of the pulse wave (142)) tends to be somewhat shorter, and is here 150 milliseconds.

Drugs (medications) alter patient physiology. Sometimes the underlying mechanisms are known, and sometimes the underlying mechanisms are not known. When the underlying mechanisms are known (or at least well characterized from an analytical perspective), then the effects of the drugs can be analyzed by decomposing the various measured signals into the underlying physiological mechanisms or known analytical coefficients. When the underlying mechanisms are less well-known, or analytical methods less adequate, alternative and more empirical methods, such as curve fitting, can instead be used to analyze patient data. Here, these hypertension examples are useful, because both analytical and empirical methods may be used.

Figure 3:
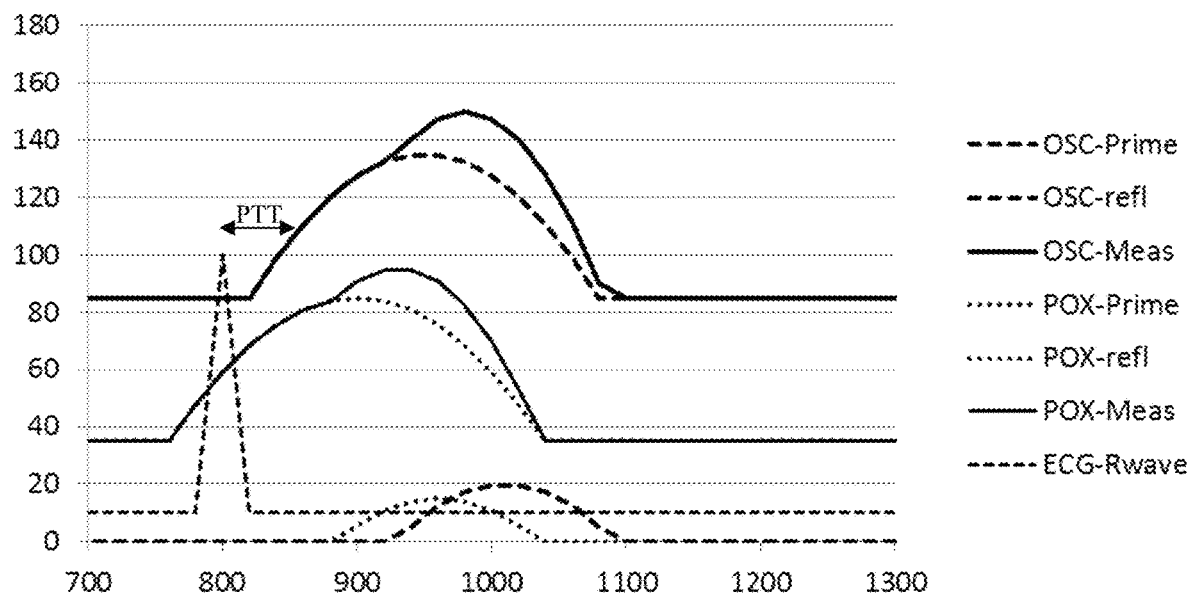
FIG. 3 shows a how a specific type medication (here type "A" medication) can impact the pulse wave measurements for the hypertension patient from FIG. 2 (above). The changes in the various and shapes of the curves can be considered to be the "impact parameter" for this type of medication. The impact parameters can be expressed either analytically in terms of the impact of the drug on the underlying patient physiology, and/or empirically in terms of the changes in the shapes of the curves (without needing to understand the mechanism by which the medication impacts the patient's physiology). Here drug "A" lowers the patient's blood pressure overall without otherwise causing much of a change in the timing of the various components of the various pulse waves.

FIG. 3 shows a simplified diagram showing, with respect to FIG. 2, the medication impact parameter for older hypertension patent 2 for a "type A" specific type of medicine. Assume in this example that this medication lowers both the patient's systolic and diastolic pressure by a certain amount (here assume 10 mm Hg for both values), but otherwise does not alter other cardiovascular parameters. Thus FIG. 3 generally resembles FIG. 2, except that the systolic (138) and diastolic values (136) are both 10 mm Hg lower.

Figure 4:
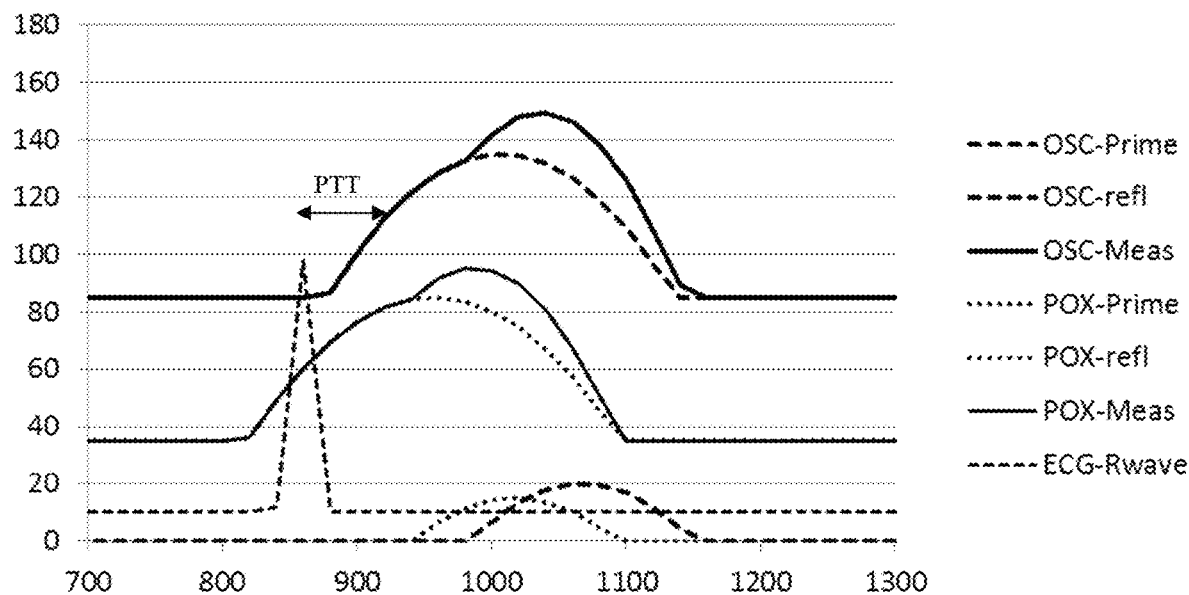
FIG. 4 shows how a different specific type of medication (here type "B" medication) impacts the pulse wave measurements for the hypertension patient from FIG. 2 above. Here drug "B" has altered the timing of the ECG "R" pulse, and has also lowered the blood pressure overall.

FIG. 4 shows a simplified diagram showing, with respect to FIG. 2, the medication impact parameter for patent 2 for a type "B" specific type of medicine. Assume that this medication reduces the patient pulse rate from 75 beats per minute to 70 beats per minute, and the beneficial effects of this medication also reduce the systolic and diastolic values by about 10 mm Hg each (down to 150/85) but otherwise do not impact the other cardiovascular parameters. Here, drug "B" has not only lowered the systolic (138) and diastolic (136) blood pressure readings by about 10 mm Hg each, but it has also changed the timing of the ECG "R" pulse (112) from 800 milliseconds to 857 milliseconds. The timing of the other pulse waveforms has also been altered accordingly.

Figure 5:
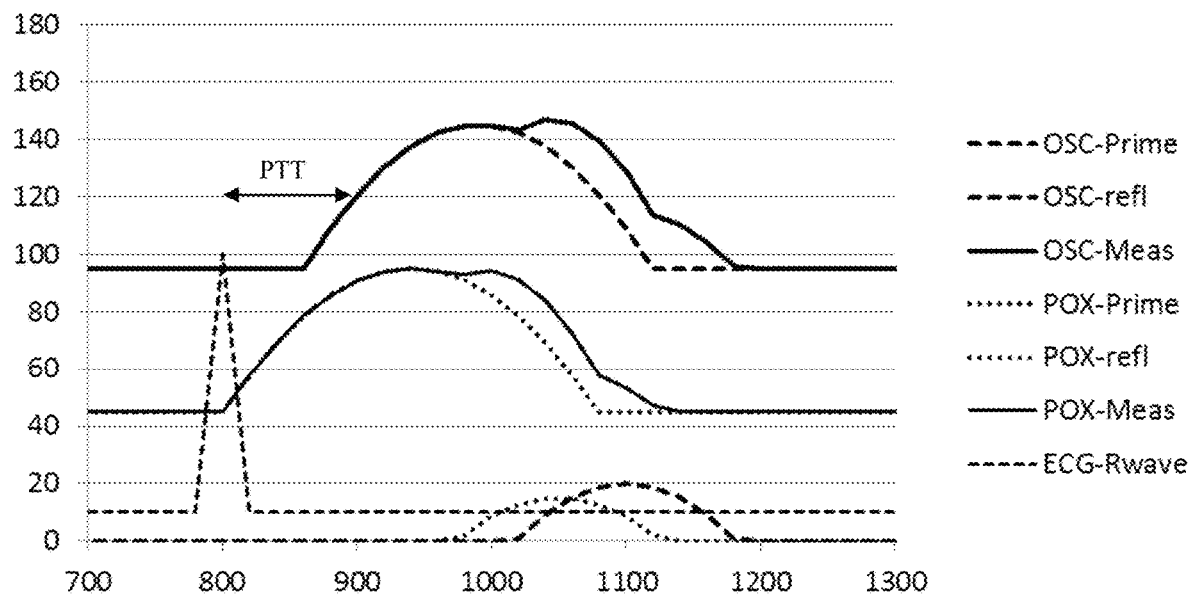
FIG. 5 shows how yet another different specific type of medication (here type "C" medication) impacts the pulse wave measurements for the hypertension patient from FIG. 2 above. Here drug "C" has done several things. It has somewhat altered the timing between the ECG "R" pulse, and the onset in the rise in blood pressure. This drug has also altered the timing of some of the various underlying pulse waves (here direct wave and reflected waves) so that they don't superimpose (augment) with each other in an unfavorable manner. This helps reduce the peak (systolic) blood pressure.

FIG. 5 shows a simplified diagram showing, with respect to FIG. 2, the medication impact parameter for patent 2 for a type "C" specific type of medicine. Assume that this medication makes the patient's arteries more flexible, and thus changes (delays) the timing for the reflected wave (s) so that the peak of the reflected wave (134, 124) does not augment the pressure effects of the peak of the primary wave (132, 122) in such an unfavorable manner. This change in reflected wave timing (say from an unhealthy 60 milliseconds to a better 110 milliseconds, or a plus 50 millisecond increase) decreases the magnitude of the systolic portion of the blood pressure (138) from 160 mm Hg to 145 mm Hg. Additionally, assume that this drug also makes the patient's other major arteries more flexible, such that the more flexible arteries have a longer pulse transit time (140) from 150 milliseconds to 190 milliseconds, for a net gain of 40 milliseconds (ms) over that patient's original baseline values (shown in FIG. 2). Thus, the time between the peak ECG "R" wave (112) and the raising part of the pulse wave (142) tends to be somewhat longer as well.

Figure 6:
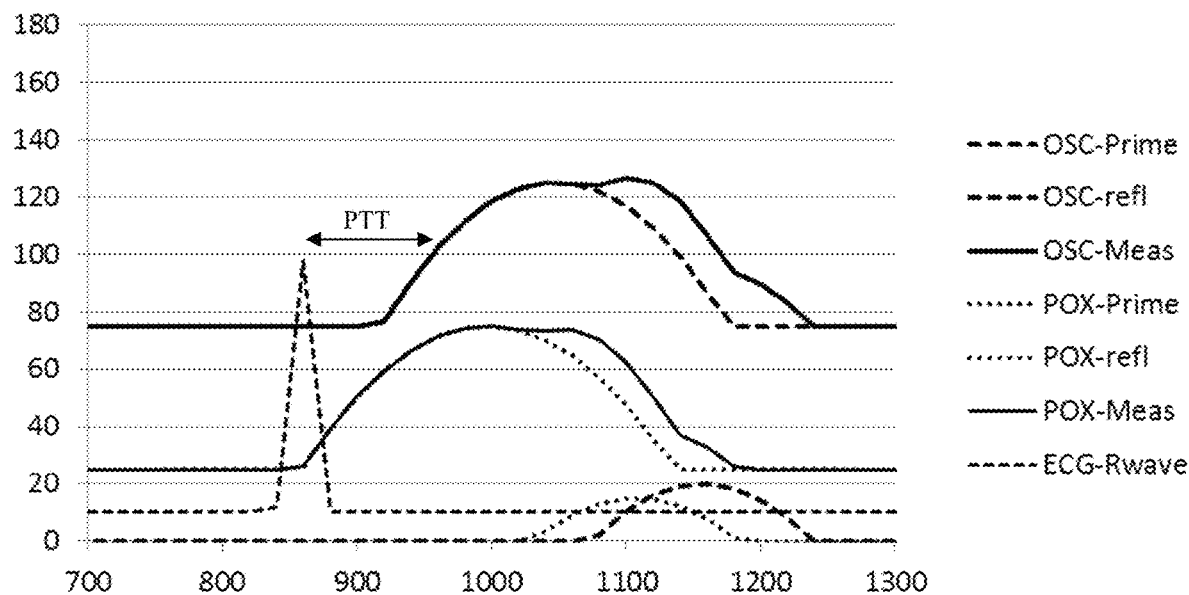
FIG. 6 shows the effect of all three medications (type "A" and type "B" and type "C") on the pulse wave measurements for the hypertension patient from FIG. 2 above. In this case, the effect of all three drugs is additive, and the hypertension patient's blood pressure is brought back to almost "normal" or acceptable values.

FIG. 6 shows a simplified diagram showing, with respect to FIG. 2, the combined medication impact parameters for patient 2 when the patient is taking all three drugs at once (e.g., drug "A", drug "B" and drug "C"). Here the three drugs all act synergistically to bring the patient's blood pressure from a formerly unacceptable level of 160/95 (systolic/diastolic) to an acceptable target level of about 126/75 mm Hg.

Here, the fact that the different types of drugs have both different underlying mechanisms of actions (on an analytical level), as well as different effects on the shapes of the patient's pulse wave data (on an empirical level) can be used by the invention to help assess if the patient is, or is not, in compliance with his or her medication schedule for these three types of drugs.

For example, we know, (and this information can be encoded into the machine's plurality of medication impact parameters) that drug "B", if taken properly (e.g., according to that patient's medication schedule information) should both slow the pulse rate (see the change in the timing of the ECG "R" wave), and also lower both systolic and diastolic blood pressure by a certain expected amount (e.g., 10 mm Hg for each). Thus, differences in pulse rate timing (e.g., the ECG "R" pulse 112) can be used to infer the presence of drug "B" using either analytical or empirical methods.

We also know that drug "C" changes the timing of the reflected wave(s) (124, 134) relative to the primary waves (122, 132). This reduces the magnitude to which the peak of the reflected wave augments the peak of the primary wave during the systolic portion of the pulse. This drug also slows down the pulse transit time (here the distance from the "R" wave to the rise of the pulse) to a more normal level, and this shows up in other waveform changes as well.

Thus, differences in the timing of the reflected waves relative to the primary waves can be used to infer the presence or absence of drug "C".

Here the analytical or empirical methods differ, however. Using an analytical approach, the shape of the measured waveform(s) such as OCS-Meas (130) and/or POX-Meas (120) could be analyzed and decomposed (e.g. using Fourier analysis) into the underlying OSC-prime (132), OSC-refl (134) and/or POX-prime (122), POX-refl (124) waveforms, and inferences as to the drug effects on the timing of the primary and reflected waves can be drawn directly.

In the analytical method, then with respect to the drug impact parameters for drug "C", the drug impact parameters could report that at this dosage, drug "C" changes the timing differences between the primary wave (132) and the reflected wave (134) by a time value such as from 60 milliseconds to 110 milliseconds, (e.g. +50 milliseconds). Thus this particular medication impact parameter, for an analytical approach, might be a simple number such as +50 milliseconds. It might also be a different number, such as an artery elasticity parameter, that might, in turn, be converted to a different time delay parameter. But in either event, we are decomposing the observed or "actual" waveforms into some underlying equations, and the medication impact parameters can report on the effects that the various drugs each have on the coefficients of the underlying equations.

By contrast, in an empirical approach, which can be more useful when the underlying mechanisms are not so well known, the medication impact parameters might instead store an average pulse waveform shape for this patient when on the drug. The empirical method might instead look at the patient 2 reference waveform (e.g., FIG. 2 OSC-Meas 130) and the pulse waveform shape assumed to occur when this patient is taking drug C (e.g., FIG. 5) and determine by curve fitting (e.g., model fitting, different types of statistical regression analysis) if the observed patient 2 data fit the drug C pulse waveform shapes above a certain significance threshold). In essence, we attempt to see how much of the actual or observed data fits a drug "C" like pulse wave profile, and how much it resembles a baseline profile without drug, and attempt to infer the presence of drug "C" without otherwise decomposing the waveform profiles into underlying equation coefficients.

In terms of analyzing combinations of drugs, note that drug "A" acts to further decrease both the systolic and diastolic blood pressure to a greater extent than would be expected by the combination of drugs "B and "C" alone. Thus, the system can also assume (or infer or deduce) that any further unexpected drop in systolic and diastolic blood pressure, not already assigned to drugs "B" and "C", can likely be attributed to drug "A".

Here, more channels of information (e.g., different types of actual patent pulse wave measurements, obtained from different sensors) are highly useful. This is because combining pulse wave measurements from at least two different types of sensors (e.g., a plurality of different types of actual patient pulse wave measurements) reduces noise, helps confirm positive signals, and can provide more insight than can any single type of measurement by itself.

It should be evident that in the examples above, any two of the various types of pulse waves will give better results than one type of pulse wave information. Thus here, combinations such as at least ECG and Oscillometric measurements, ECG and pulse oximeter measurements, or oscillometric and pulse oximeter measurements may be used. Combinations of three or more types of pulse wave data can be still more useful and accurate.

Thus, in some embodiments, the invention may be a method, device, or system for determining any of the effectiveness of a medication regimen or a patient's adherence to a medication regimen. The invention will typically comprise, or use, multi-sensor patient operable instrumentation such as that previously described in U.S. patent application Ser. No. 14/186,151 and 62/138,377, the entire contents of which are incorporated herein by reference. See FIGS. 9 and 10 for some examples. Other types of sensors and data sources may also be used.

This patient operable instrumentation will typically comprise at least one computer processor (microprocessor, microcontroller, etc.), memory (at least one of local or remote memory) and various different types of physiological monitoring devices, each configured to obtain a plurality of different types of actual patient pulse wave measurements. The instrumentation will typically be designed so that it is at least capable of operation by an average patient in the absence of a healthcare practitioner. Of course, in some cases, this instrumentation may alternatively be operable by an average caregiver who will typically not need to be a licensed or professional healthcare practitioner. The idea, in any event, is to make the invention's instrumentation convenient and easy to use so that it is used very frequently.

In a preferred embodiment, this patient operable instrumentation and its various physiological monitoring devices will be configured to provide various different types of actual patent pulse wave measurements. Preferably at least two different types of pulse wave measurements will be obtained. For example, these various types of patient pulse wave measurements can include oscillometric pulse oximeter data (e.g., pulse waves that report on varying blood oxygen saturation levels), electrocardiograph (ECG) readings, and pulse waves that report on blood pressure measurements (e.g., oscillometric measurements from a cuff or non-cuff type device).

In a preferred embodiment, the patient operable instrumentation will not consist entirely of independent stand-alone monitoring devices. Instead, at least some and preferably all of the monitoring devices will form a unitized system where all devices are managed by at least one common processor, preferably at least one common processor local to the patient operable instrumentation. Here again, see the patient operable instrumentation shown in FIGS. 9 and 10 as specific examples. This patient operable instrumentation will typically be referred to as "the device" for these discussions.

In order to determine if a patient is adhering to a particular medication, or if a particular mediation is having the expected effect on the patient's physiology, the device, system, or method will, in addition to patient baseline physiological data (e.g. data in the absence of drugs/medication) also need to know the patent's medication schedule information (e.g. what drugs is the patient supposed to take, and when) and the expected impact of these drugs (or at least the drugs where monitoring is desired) on the various patient physiological parameters. For example, if a patient's doctor prescribes medication A, B, and C every day, the patient medication schedule information is essentially the prescription to take mediations A, B, and C every day. Medication schedules vary by number of drugs and number of times per day, often differ between patients, and are customized for particular patients.

Thus, the invention will typically be configured to store and retrieve a variety of different types of information. This information can include medication schedule information that pertains to at least one medication and medication dosing schedule for at least one given patient. For the patient shown in FIGS. 2-6, for example, this can be a list or simple record stored in computer memory showing that this patient takes drugs "A", "B", and "C" on a daily basis, usually around 9:00 pm. Thus, the device, for example, can store medication schedule information pertaining to at least one medication and medication dosing schedule for that patient.

TABLE 1

Medication schedule information example

| Drug | Days | Times |
|---|---|---|
| A | Daily | 9:00 pm |
| B | Daily | 9:00 pm |
| C | Daily | 9:00 pm |

The invention will also typically store a plurality of medication impact parameters. Here each individual medication impact parameter provides information on how a specific medication alters a specific type of pulse wave measurements. Here various types of data can be stored and used depending on if the system processor is going to be using either an analytical approach, an empirical approach, or both approaches. An example of the medication impact parameters for drugs "A", "B", and "C" on a patent similar to that shown in FIGS. 2-6 is shown below:

TABLE 2

Medication impact parameters example

| Drug | Δ ECG-R | Δ PTT | Δ Reflected | Δ systolic | Δ diastolic | Waveform example(s) |
|---|---|---|---|---|---|---|
| A | 0 | 0 | 0 | −10 mm/Hg | −10 mm/Hg | FIG. 3 curves |
| B | +57 ms | 0 | 0 | −10 mm/Hg | −10 mm/Hg | FIG. 4 curves |
| C | 0 | +40 ms | +50 ms | computed | computed | FIG. 5 curves |

In this case, an "individual medication parameter" corresponds to a single row in the above list or record stored in memory, and the plurality of medication impact parameters corresponds to the above table as a whole.

The invention will also store a plurality of patient reference information, where each individual patient reference information provides information on a specific type of patient baseline pulse wave measurements in an absence of a specific type medication. For the patient in FIG. 2, the patient baseline information in the absence of all medication can include, for example, all of the information shown or discussed in FIG. 2.

According to the invention, at least one processor (preferably at least one local device processor, but alternatively also may be a remote processor) is configured so that when the patient operable instrumentation is used on the patient, this at least one processor will analyze the plurality of different types of actual patient pulse wave measurements. Here the processor will know what time this analysis is done relative to the medication schedule information. This time information can be used to adjust the analysis accordingly. Thus, the processor may be configured so that if the readings are taken just before the patient was scheduled to take the medication, then any aberrant readings can be discounted. However, if the readings are taken at several hours after the medication was expected, and aberrant readings are still obtained, then the aberrant results may be given a correspondingly higher weighting and be reported accordingly.

The invention will then use at least one processor to determine which of the various actual patient pulse wave measurements are inconsistent with calculated patient pulse wave measurements that the system would normally expect for that patient. This calculation is based on the medication schedule information, the time (here time means time and the date) the actual data was taken, the various patient reference information, and the various medication impact parameters.

The invention can then do various things with the results, in a preferred embodiment varying depending on what is found. The invention may just store the findings in memory, or inform the patient, or inform caregivers, or inform relevant healthcare professionals, or keep human readable records. At a minimum, however, the invention will least store a record in the invention's memory (either local and/or remote) of at least those medications where inconsistent findings were found (e.g., evidence that the patient was not responding to the medication as would be expected).

In a preferred embodiment, the invention's at least one processor may be further configured to provide patient alarm information. This patient alarm information could report when various patient physiological parameters, such as when the patient's blood oxygen saturation, blood pressure measurements, electrocardiograph readings, or other sensor readings fall outside of previously established boundaries. The invention may also be configured so that the device uses this patient alarm information, as well as those medications where inconsistent findings were obtained, to determine and report that the patient may either be out of compliance with taking these expected medications or that the medications are not acting as anticipated.

Such alarms can, in principle, be produced when an inconsistent result is obtained from only one type of measurement of a single patient physiological parameter (e.g., just blood pressure, just pulse) and only one drug (e.g., only one anti-hypertensive mediation) is used. However, the true value of the invention is most apparent in more complex situations, where the patient is taking a plurality of medications, and a plurality of patient physiological parameters are measured, and the system is thus solving for multiple unknowns (effectiveness of drug a, drug b, drug c . . . ) using multiple variables (not only variables between one type of physiological parameters, but also variables between different types of physiological parameters).

Value of Combining Different Types of Pulse Wave Measurements:

In a preferred embodiment, the invention will use its at least one processor to determine if inconsistent findings were obtained over more than one different type of actual patient pulse wave measurements. For example, do the blood pressure and pulse oximeter findings agree? Are any of these results consistent with the ECG results? Here the invention can be configured so when at least two different types of actual patient pulse wave measurements both report inconsistent findings (i.e., both report a possible medication effectiveness or adherence problem, so both are consistent with each other), the device can more definitively determine and report that the patient may be out of compliance with taking those particular medications.

Methods of Obtaining Medication Impact Parameters:

In general, any method of obtaining the medication impact parameters may be used. Here, however, although the gold standard would almost certainly be experimenting on the patient by selectively withholding all medications, and then introducing one at a time, and monitoring results, this method will often not be practical. This is because both doctors and patients may (quite properly) object to deliberately withholding important medication. Thus, various substitute methods will often be needed in order to obtain the medication impact parameters in a safer and more ethically responsible way.

Often methods that attempt to estimate the mediation impact parameters based on the patient's data in the known presence of adequate medication, as corrected by the typical known effects of a given medication may be used. Here the probable changes in the various patient waveforms caused by the various drugs can be calculated, and these values used for the medication impact parameters. This is not as good as performing the unethical experiment, but better than nothing.

In some embodiments, these various medication impact parameters can be obtained by taking averages over a plurality of similar type patients in the presence and absence of a given medication (here results from clinical studies may be used), and the differences between the various pulse waveforms in the presence and absence of a given medication can be calculated based on such clinical study data. Again, this is not as good as performing unethical experiments on the actual patient being monitored, but better than nothing.

Similarly, the various types of patient reference information (e.g., various pulse wave waveforms in the absence of drugs) may be obtained by averaging over a plurality of similar type patients in the absence of the various medications. Here again, data from clinical studies may be used. Alternatively, various mathematical models may be used. Again, not as good as performing unethical experiments on the actual patient being monitored, but better than nothing.

As will be described later on in this disclosure, the invention may also be configured so as to take advantage of "natural experiments" when the patient has forgotten to take one or more medications to ethically obtain more accurate patient reference information.

In some embodiments, the invention may be configured so that the device's at least one processor calculates the expected patient pulse wave measurements from the previously stored medication schedule information (and the time), a plurality of patient reference information, and a plurality of medication impact parameters. Here the invention can use its least one processor to transform the plurality of patient reference information into the expected patient pulse wave measurements by various mathematical operations. For each individual medication (as expected from the medication schedule information), these operations can include:

1: selecting corresponding individual medication impact parameters from list or record of various medication impact parameters, thereby retrieving the selected individual medication impact parameters.

2: Applying (using either analytical methods based on underlying equations that attempt to reproduce aspects of the patient's physiology, or by empirical curve fitting methods), these selected individual medication impact parameters to the various patient reference information, thereby producing intermediate transformed patient reference information. For example, if the patient reference information is as shown in FIG. 2, then applying drug "C" to this patient reference information would produce the results shown in FIG. 5, and so on.

3: Repeating the above steps until all of the individual medication (drugs) in the medication schedule information has been processed, thereby producing the expected patient pulse wave measurements. For example, going down through the list, and applying drug "A", drug "B", and drug "C" to the patient reference data from FIG. 2, thus producing FIG. 6. If the actual patient data resembles FIG. 6, and the timing is appropriate, then the patient is probably taking all three drugs. If the actual patient data does not match, the invention can then alternatively try further by seeing if any partial combination of drugs fits the observed data. The system can then report on its findings (based on which combination of expected drugs best fits the observed data, and which deficiency in the combination of expected drugs best fits the observed data.)

Other Types of Medication and Patient Monitoring Sensors:

Although for simplicity, much of the discussion so far has focused on pulse wave measurements and anti-hypertension drugs, it should be evident that the concepts disclosed herein may be used for a broader range of patient physiological measurements and a broader range of drugs as well, In some embodiments, the invention may be further configured with additional types of sensors. These sensors could include one or more additional types of sensors such as body temperature sensors, patent motion sensors (e.g., accelerometers), lung function sensors (e.g., microphones, spirometers), ECG electroencephalographic (EEG) sensors, and the like. In these embodiments, the various categories of stored information would be extended to accommodate these additional types of physiological data, drug types, and medication impact data.

For certain types of sensors, such as motion sensors, and blood glucose monitoring data, common devices, such as smartphones (e.g., smartphone motion sensors) and blood glucose monitors are inexpensive, widely available, and often carried by patients throughout the day. These smartphones and blood glucose monitors are often configured to deliver their data via various wired or wireless (e.g., Bluetooth, Wi-Fi) computer links, upon demand. In some embodiments, the invention may be configured to retrieve such motion sensing data, blood glucose monitoring data, and the like, store them in the invention's database, and use this information to help supplement information taken from the invention's own sensors.

Thus, for example, the patient reference information data would be extended to further comprise baseline body information pertaining to these additional types of sensors. This can be, for example, at least one of baseline body temperature information, baseline patient motion data, baseline patient lung status data, baseline patient blood glucose levels, or baseline patient EEG data.

In some embodiments, the patient reference information data may be further extended to also comprise the patient's baseline (or "normal") drug response information (here called baseline-drug-response) pertaining to how the patient's body normally responds to the various drugs, as determined by the various sensors. This can be, for example, at least one of baseline-drug-response body temperature information, baseline-drug-response patient motion data, baseline-drug-response patient lung status data, baseline-drug-response patient blood glucose levels, or baseline-drug-response patient EEG data. Generalizing the patient reference information to further include how the patient would be expected to normally respond to drugs (at least in the absence of adverse drug interactions, other changes in the patient's medical status, and the like) helps the system better determine situations where the effectiveness of one or more drugs may be compromised.

Similarly, the individual medication impact parameters can be extended to further provide information on how a specific medication alters at least one of these additional types of sensor data, such as baseline body temperature information, baseline patient motion data, baseline patient lung function, patient motion, patient blood glucose levels, and patient baseline EEG data.

In these embodiments, the invention's at least one processor can be further configured to use this (suitably extended) medication schedule information, the known time of data acquisition, the various patient reference information and at least some of the individual medication impact parameters to further determine if at least some of these additional (e.g. non-hypertension) medications are also producing inconsistent findings (e.g. provide evidence that the patient is also not adhering to this additional medication as well).

In some embodiments, the invention can be configured to determine any of drug effectiveness and/or patient adherence to a medication regimen using these inconsistent findings. Note that "using" these inconsistent findings does not imply "using only" these inconsistent findings. Further, the system may be configured to use its at least one processor to establish or refine this effectiveness based on the patient's medication adherence. Alternatively, or additionally, the system may be configured to output multiple scenarios, such as patient not adhering to the mediation regimen and/or the mediation is not acting effectively. In such scenarios, the system may be configured to use its at least one processor, or a remote processor, to query the patient, the patient's caregiver, or automated pill dispensing or monitoring devices, and use such outside medication adherence information to further refine system estimates that the mediation may not be acting effectively. The system may also be further configured to query the patient or caregiver as to changes in the timing of drug administration, changes in the patient's diet, changes in any patient nutritional supplements, or changes in patient health status (e.g., recent illnesses), and use this additional information to further determine if the present patient medication regime is not acting effectively in the real world.

Figure 7:
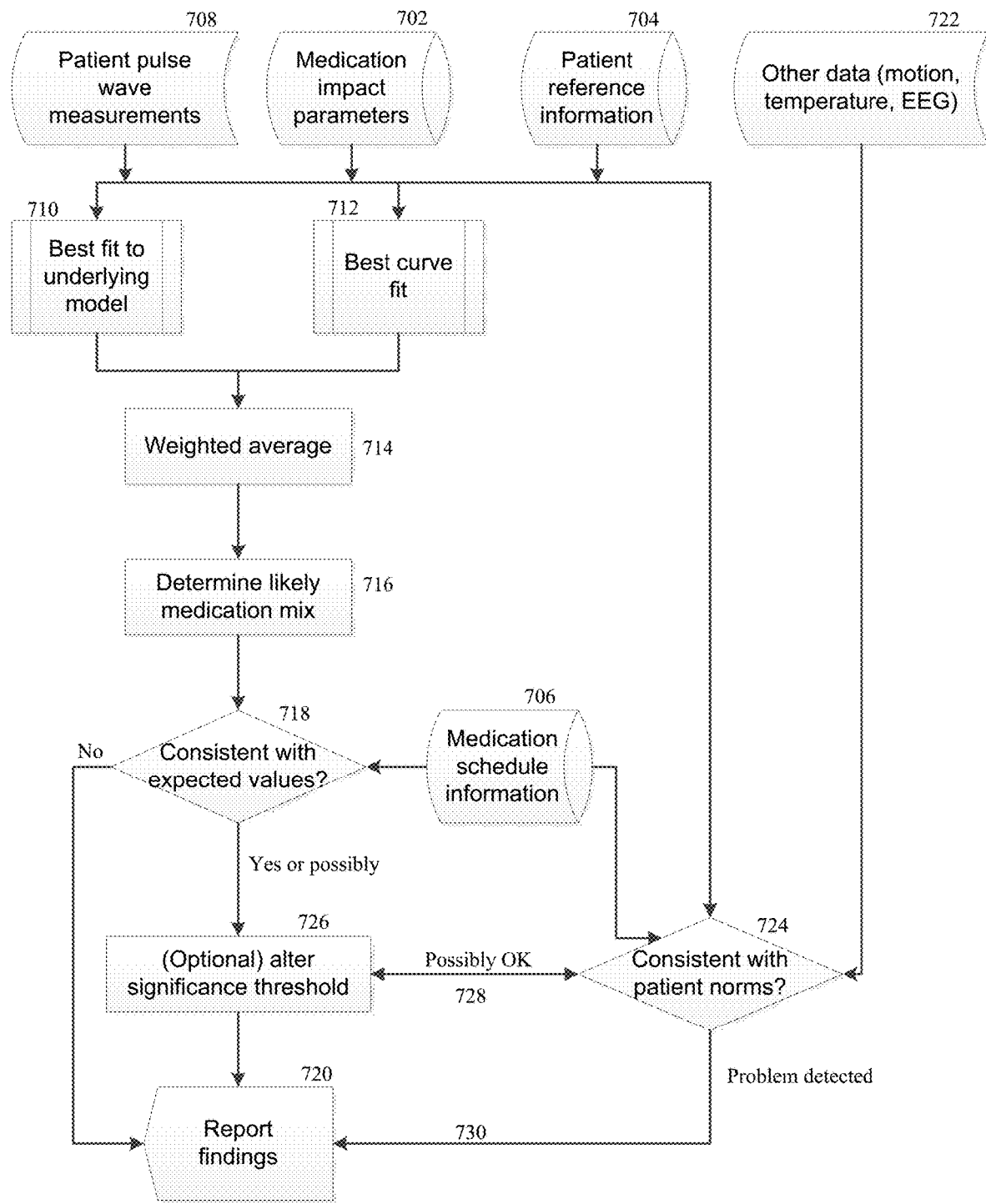
FIG. 7 shows a flow chart showing of some of the various steps that may be carried out by the medication effectiveness/adherence device's processor in order to determine if the various physiological measurements taken by the device's various sensors are showing that the patient is likely following his or her assigned medication schedule, or not.

To better visualize these various steps, processes, and methods, consider FIG. 7. FIG. 7 shows a flowchart of some of the various steps that may be carried out by the device's processor. Here the patient's various medication impact parameters (702), which report on how each individual medication taken by the patent alters a specific type of pulse wave measurements, are stored in memory. Additionally, patient reference information (704), which provides information on an individual patent's pulse wave measurements in the absence of either all medications, (exemplified by FIG. 2), or in the absence of at least some medications, are also stored in memory. The patient's medication schedule information (reporting on which medications the patient is taking, and when (e.g., the dosing schedule) is also stored in memory (706).

When the patient operable instrumentation and its plurality of physiological monitoring devices (here exemplified by patient pulse wave data such as rapidly time varying blood oxygen saturation levels (e.g. using a pulse oximeter type sensor), blood pressure readings (e.g. using an oscillometric type blood pressure sensor), and electrocardiograph readings (e.g. using one or more ECG electrodes) is taken, this data is also stored in memory as well (708) as a series of different types of pulse wave measurements.

Once the patient pulse wave measurements (data) have been obtained, the invention will then use at least one processor to analyze this data. As previously discussed, there are two general approaches that can be used here, and the invention may use either approach or both approaches.

In a first, more analytical approach, the invention's processor(s) will attempt to analyze the various patient pulse wave measurements according to one or more analytical models. Using cardiac pulse waves as an example, examples of such analytical models can include, but are not limited to, models such as Moens-Korteweg equation, the Bramwell-Hill equation, the Waterhammer equation, Windkessel theory, and the like. The invention's processors may attempt to obtain fundamental values such as the time differences between cardiac forward waves and reflected waves, systolic and diastolic blood pressure, pulse transit times (PTT), pulse wave velocities (PWV) and the like. This is shown in (710).

In a second, more empirical approach, the invention's processor(s) attempt to analyze the various patient pulse wave measurements according to a best fit to underlying basis curves approach (712). Here, the invention will draw upon various underlying pulse wave curves that describe the patient's pulse waves according to the effect of each different type of drug on that patient's baseline (e.g., in the absence of all drugs) profile. When this option is used, the underlying patient pulse waves may be stored in memory as well. Here, for example, the patient baseline curves may be stored as either part of the patient reference information (704), while the empirical impact of various drugs on that patient's various types of pulse waves may be stored along with the medication impact parameters (702). Other data storage schemes can also be used.

Although the invention may use either the model based (710) or the empirical approach (712) on a stand-alone basis, in a preferred embodiment, which may have the advantages of being more noise resistant in some cases, the invention may determine which approach fits the underlying data best, and then combine the results from both approaches to produce a weighted average of the two. Here, the approach that fits the underlying data the best (best fit may be determined by a least-squares approach or other best fit determination algorithm) may be given a higher weight. This optional but preferred embodiment is shown as (714).

Using either approach, the invention will then determine which likely mediation mix best fits the available pulse wave data (716).

In step (718), the invention's processors will then compare the observed medication mix information (716) with the medication mix expected from the patient's medication schedule information (706). The processor may employ various rules or rubrics to help implement this comparison process. For example, the processor may use rules such as, "the patient is likely to take all medications at once, or skip all mediations" in this analysis. The medication impact parameter information (706) may further contain information regarding the half-lives of the various drugs. Thus, for example, if a patient stopped taking all medication, the effects of the drug with the shortest half-life would diminish first, and the effects of the drugs with longer half-lives would diminish later.

If in step (718), the pulse wave results are clearly inconsistent with the medication schedule information (706), then the analysis can clearly determine already that there is a problem, and report it at step (720) (or at least store this in memory, and preferably also notify a person or machine).

In some embodiments, the invention may further double check its apparently OK results, and/or or alternatively report other types of potential medication problems. In these embodiments, the invention may often monitor other types of physiological parameters as well. For example, the patient operable instrumentation may be further configured to include other types of sensors, such as accelerometers (particularly useful for patient worn instrumentation), patient temperature sensors, electroencephalographic (EEG) reading sensors, breathing status sensors (stethoscope-like microphones and sound analysis algorithms, spirometer sensors), and the like. This other data from the other types of sensors will be stored in memory as (722).

In this "extended other data" embodiment, the patient reference information (704) may further include information pertaining to this "other data", such as information pertaining to the patient's typical motion (e.g., does the patient tend to shake or move in an atypical manner), typical body temperatures, typical EEG waveforms (e.g., example baseline waveform for a patient with epilepsy), breathing parameters (e.g. respiratory data pertaining to conditions such as asthma) and the like. This can not only act as a double check to help insure that any cardiovascular drugs are being adequately monitored, but can also be used to extend the variety of different types of drugs and medical conditions that can be successfully monitored by the invention.

Although in some embodiments, the invention can be configured to determine respiration rate directly from respiration sensors, in other embodiments, the invention can be configured to infer or calculate respiration rates based on other measurements. For example, during respiration, there are typically characteristic changes to the pulse, ECG, blood pressure, pulse oximeter data (e.g., photoplethysmogram/PPG data) and the like. The pulse tends to slow down, and blood pressure tends to also drop on a frequency that varies according to respiration rate. Thus, in some embodiments, the invention can use various computational methods, such as Fourier analysis, to mathematically determine breathing rates from any of the ECG, pulse oximeter, oscillometric data used for blood pressure determination, and/or other sources.

Here the medication impact parameters (702) and medication schedule information will also typically be extended to report on the impact of these other types of medications on the patient, as well as report on the schedule by which the patient takes such other types of drugs.

For example, consider a patient with epilepsy or Parkinson's disease. Here, improper epilepsy or Parkinson's medication may not show up in the patient's pulse wave measurements, but may show up as either abnormal motion data (e.g., patient trembling, patient abnormal motion) or as abnormal EEG readings or even abnormal temperature readings.

At the same time, patients with other ailments, such as epilepsy or Parkinson's disease, are hardly immune from common high blood pressure and other cardiac difficulties. Thus, in some embodiments, it is useful to have the same patient operable instrumentation monitor drugs directed towards completely different types of disease states.

In some other types of disorders, in particular breathing or lung disorders (e.g. (asthma, chronic obstructive pulmonary disease, other chronic lung disorders), the underlying medical condition and the various medications used to treat the lung disorder, can interrelate with the patient pulse wave measurements. Thus, in these embodiments of the invention, the invention will also simultaneously evaluate these other factors as well.

Consider the case where the patient's other (non-pulse wave) data (722) is also inconsistent with the patient's typical reference information (704) for this other type of (non-pulse wave data). This consistency can be checked at step (724). The relationship between findings obtained from this other (non-pulse wave) data at step (724) and the pulse wave data findings (718), and the medication schedule information (706) can help with the analysis of both types of data.

For example, given that on a statistical basis, a patient that has forgotten one type of medication is also more likely to forget to take another type of medication; findings of abnormal pulse wave values tend to make other types of abnormal data more significant. Similarly, findings of abnormal non-pulse wave data tend to make findings of abnormal pulse wave data more significant.

Other drugs may also be monitored according to the invention, including:

Other cardiac drugs, such as ivabradine (Corlanor®), which acts to block the mixed sodium and potassium membrane channel (HCN) channel in certain cardiac pacemaker cells (sinoatrial SA node tissue). This inhibits the cardiac $I_f$ current, and lowers the heart rate. Specifically the drug slows the diastolic depolarization, and thus its effects can be seen by changes in the ECG pulsewave signal, along with other effects such as a lower pulse rate. It has certain side effects, such as very slow heart rate (bradycardia), hypertension (high blood pressure), and can also cause atrial fibrillation, ventricular fibrillation, prolonged ECG QT intervals, dizziness and weakness which the patient may also report. In some embodiments, the system may also issue user warnings not to take the medication if their blood pressure is too low (e.g., less than 90/50), or if their heart rate is too low (e.g., <60 bpm), or if the ECG detects heart block or prolonged QT intervals.

Neprolysin inhibitors drugs such as sacubitril (sold as the sacubitril/valsartan combination drug Entresto®), work by inhibiting an enzyme (neprilysin) that normally degrades vasoactive (natriuretic) peptides, resulting in a higher level of these vasoactive peptides, and is thus useful for treating heart failure and related cardiovascular problems. These drugs have certain effects, and side effects, and adverse drug interactions that can be detected and reported by the invention, including hypotension (low blood pressure), hyperkalemia, and cough (which could be detected by either a patient survey, or by monitoring patient cough using a microphone (either built-in, or located on another computerized device such as a smartphone) and suitable cough analysis software, such as the software disclosed in U.S. Pat. No. 9,526,458, the entire contents of which are incorporated herein by reference).

Diabetes drugs and complications, including:

SGL2 inhibitors (sodium-glucose co-transporter 2) inhibitor drugs, such as canagliflozin, dapagliflozin, empagliflozin, ertugliflozin, ipragliflozin, and the like are used to improve glycemic control in type 2 diabetes. The human kidney operates by first excreting nearly all small molecules (such as glucose), but then using specific transporter proteins to then re-absorb important small molecules. The SGL2 inhibitors interfere with this reabsorption, causing excess glucose to be excreted from the body. Unfortunately, these drugs can have various serious side effects, such as kidney failure, hyperkalemia, hypotension, ketoacidosis, and the like.

Here, at least some of these side effects can manifest themselves by changes in pulse wave data and other sensor information, such as lower blood pressure, elevated heart rate, and altered ECG data. Additionally, data imported from other sensors, such as blood glucose sensor data, can also be used by the system to help determine if the patient is either developing an undesirable side effect to the SGL2 inhibitor, has adverse drug interaction issues, or is simply noncompliant with one or more drugs.

GLP-1 analogs (glucagon-like peptide 1 receptor agonists) drugs, such as albiglutide, dulaglutide, exenatide, liraglutide, lixisenatide, and semaglutide are also used to help treat type 2 diabetes. These drugs act to enhance pancreatic glucose-dependent insulin secretion, which is often deficient in type 2 diabetics. These drugs also have their own side-effects including increased heart rate, lowered systolic and diastolic blood pressure, as well as characteristic changes in ECG profiles such as changes in the ratio between low and high frequency components (LF/HF ratio). Here again, data imported from other sensors, such as blood glucose sensor data, can also be used by the system to help determine if the patient is either developing an undesirable side effect to the GLP-1 analogs, has adverse drug interaction issues, or is simply noncompliant with one or more drugs.

The invention can also be used to investigate drug related problems that result in symptoms of diabetic ketoacidosis (DKA), which can be a drug related complication of diabetes, results in changes in serum electrolytes (e.g., hypokalemia) and other problems that can result in characteristic ECG differences, such as abnormal repolarization patterns, prolonged QT intervals and the like. Additional problems are abnormally high glucose levels (here blood glucose data can be imported by the invention), nausea (which can be reported using a patient interview interface), trouble breathing (which can be directly or indirectly monitored) and the like. Here again, the system can review a profile of the various drugs that the patient should be taking, and attempt to determine which drugs or drug interactions may be causing these symptoms. Sometimes the problem may be a simple deficiency of insulin, but other times the problem may be caused by a more complex drug interaction issue, and here the invention can be particularly useful in this later situation.

Narcotic opiate antagonists for weight loss include drugs such as Contrave® (a naltrexone bupropion mixture) which can be taken over a period of time to assist in weight loss. This type of drug can have various types of side effects and adverse drug interactions, some of which manifest as ECG changes (QRS prolongation) and cardiac arrhythmia. The drug also has certain adverse drug interactions with other drugs, such as MAO inhibitors (blood pressure increase, heart palpitations, tremors), CYP2D6 inhibitor drugs (may cause irregular heartbeat), and other medications. Here again, the invention can be used to monitor if the combination of drugs that the patient is taking is effective, or if the patient is obtaining ineffective results (either due to noncompliance, adverse drug interactions, unexpected physiological issues, and other causes).

Opioids, Opioid Antagonists, and Pain Management Methods

Opioids, which are commonly and legitimately used for medical pain management purposes, are also notoriously abused to the point where this has become a major public health crisis in the US and elsewhere. It can no longer be assumed, for an example, that an average patient who may be taking a plurality of prescribed drug medications is not also taking an undocumented opioid drug as well, or a prescription opioid at too high a dose. Thus, undocumented opioid use can create unanticipated adverse drug reactions. Such adverse reactions can show up as abnormal (prolonged) ECG QT intervals, ventricular arrhythmia, respiratory depression, and other signals that can be detected by the invention.

In some embodiments, the invention's algorithms may be configured so as to attempt to fit data according to a model where the patient (user) is, in addition to the prescribed drugs, also taking one or more drugs of abuse, such as various opioid drugs according to an undocumented drug of abuse mediation schedule. Thus, the invention may be configured to determine if a good fit between the patient's official medication schedule, known medical conditions, and invention sensor data, can be obtained by also assuming such an undocumented drug of abuse schedule. Although this is clearly sensitive information, the invention may also be configured to warn the patient, or the health care practitioner, or others when such a fit has been found. If nothing else, the system can at least warn the patient about the risks of taking drugs of abuse when such a fit occurs.

Additionally, even when the opioid drug is being used according to the official medication schedule, the system can of course also inform when the opioid is causing adverse drug reactions or adverse drug interactions, or otherwise interfering with the effectiveness of the patient's medication regimen.

Opioid antagonists: Certain opioid antagonists, such as Narcan® (naloxone HCL) are often used to help reverse opioid overdoses. Here the invention may also be used to determine when Narcan should be used, if an effective dose of Narcan has been administered, and if additional medical support, such as CPR, rescue breathing, and the like are indicated. Additionally, the system can warn about side effects of Narcan (e.g., sudden opioid withdrawal symptoms) and can warn accordingly as well.

Patient Controlled Analgesia (PCA) Devices:

Patient controlled analgesia (PCA) devices are commonly used to assist in patient pain management. They generally comprise computerized syringes or IV pumps that are often set to deliver a lower volume of pain medication (often an opioid drug) to a patient's IV line, but which can also be configured to allow the patient to increase the amount of medication (usually by pressing a button) to help the patient better manage periods where the pain is more intense. To prevent accidental overdose, the PCA computer is configured to limit how much pain medication the patient is allowed to self-administer. Examples of such systems include Boydman, U.S. Pat. No. 5,069,668, and Bollish U.S. Pat. No. 5,957,885, the entire contents of both of which are incorporated herein by reference.

In some embodiments, the devices and methods of the present invention may be used as part of a PCA control system. Here, for example, the invention may be used to continually monitor patient vital signs in the context of all medication that the patient is receiving, and in the context of the patient's overall medical condition. Input from the invention as to possible adverse drug reactions can then be used to automatically adjust any of either the PCA baseline settings, or limits on the amount of drug medication that the patient is allowed to self-administer. These methods and systems can be particularly useful in situations where the patient is in intense pain, and is pushing the safe limits of drug use.

The invention may also be used to monitor or detect other signatures for adverse drug interactions as well.

Some other signatures of adverse drug interactions include prolonged ECG QT intervals, as well as a trending low blood pressure (often caused by unfavorable drug interactions). Here again, the invention can use the sensor data, and knowledge of the patient's drug schedules, to detect an alert such trends, hopefully before severe symptoms begin.

Due to measurement noise and general physiological variability, often the invention's methods may not produce results are entirely clear cut. Instead, the invention will typically obtain compliance or effectiveness data that is best expressed in a more probabilistic numeric score, in which the system may judge, for example, that the probability that a patient is in compliance or that a given drug is effective, such as drug "C", at any time is a probability number, such as 70%.

In some embodiments, data obtained from the non-pulse wave "other" data may be used to change the weighting or significance level that the system uses to interpret its findings and report results. A patient with a borderline pulse and blood pressure data, as obtained from the pulse wave data, may be more likely to be scored as non-compliant with the medication schedule information if the patient is also exhibiting breathing problems, and vice versa. Thus, in some embodiments, it may be useful to compare findings between the pulse wave and non-pulse wave wings of the analysis and use this comparison to alter (728) the significance threshold (726) by which the system reports problematic findings. This option (728) may be most useful when the significance of any abnormal findings is somewhat uncertain. If it is very clear that abnormal patient physiological parameters are being detected by the "other data" wing (722, 724), then these clearly abnormal results may be reported immediately (730). Here, the medication schedule information (706) may be used to suggest which medications may be at issue here.

Reporting Findings, and Interfacing with Remote Network Connected Devices:

In some embodiments, the invention may further be configured with means (e.g., touch screens, buttons, voice interface, network interface) to receive compliance information from the patient. Here the patient (or caregiver) can also report on periods when it is known that the patient was out of compliance with at least one known medication. This, in essence, constitutes an ethical "natural experiment" that can be used to obtain further calibration information for the invention. To take advantage of this ethical "natural experiment', the invention's at least one processor can be further configured to use this compliance (or lack of compliance) information to select at least some of the actual patient pulse wave measurements for use in establishing or refining at least some of the patient's medication impact parameters and/or the patient reference information.

Say that the patient has forgotten all medications for several days. Here the system can at least take advantage of this unfortunate fact and gather more accurate patient reference information.

In some embodiments, the invention may be further configured with network interface means (e.g., WIFI or Bluetooth™ or wired or other type of computer network interface) to allow the invention to connect with at least one remote computerized device over a network (preferably a computer network). Here the invention's at least one processor can be further configured to report at least some of those medications where inconsistent findings were obtained to a remote computerized device (e.g., a caretaker device, a patient smartphone tablet, or computer device, a healthcare professional computerized device, and so on).

In these embodiments, the invention's at least one processor can be further configured to enable any of the various medication impact parameters, patient reference information, and medication schedule information to be uploaded or downloaded over a network from a remote computerized device. Here, for example, a healthcare professional, upon prescribing a new medication, might also contact the invention and upload the medication, preferred use schedule, and medication impact information to the invention so that patient compliance and/or drug effectiveness can then be monitored.

Note that more specifically, and as previously discussed, according to the invention, effectiveness can also be viewed as comprising an impact of at least one specific medication on a patient's actual patient pulse wave measurements, as compared to calculated expected patient pulse wave measurements, for a medication regimen comprising a plurality of drugs that the patient is expected to take.

In some embodiments, the invention may also be configured to, either directly, or by way of other computerized devices such as wirelessly connected smartphones, tablets, and the like, query the patient regarding changes in the patient's health status. Thus the patient can, in some embodiments, input useful information such as reporting nausea, sweating, trembling, changes in urination, and other symptoms that the system may incorporate into its various decision algorithms.

Figure 8:
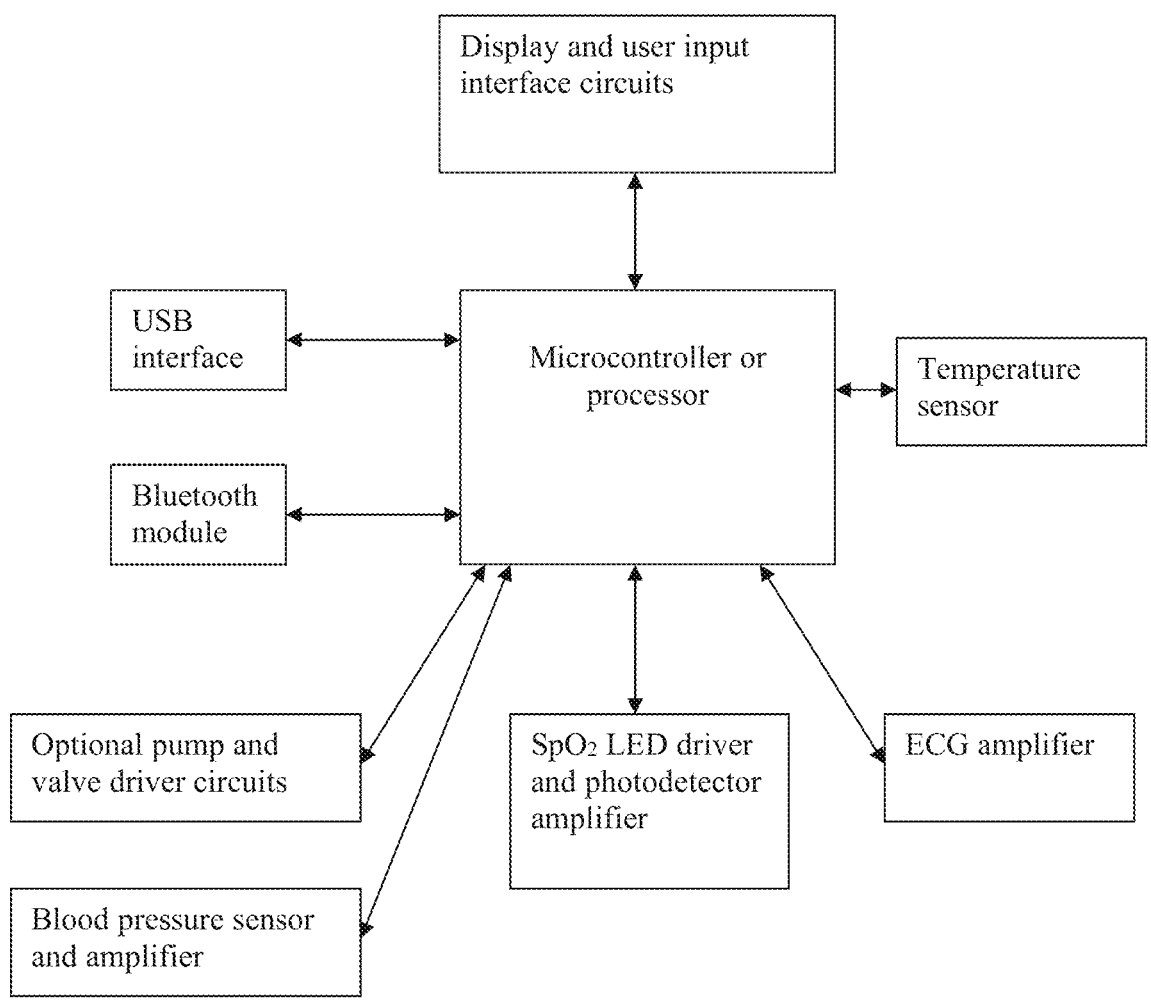
FIG. 8 shows an example of one type of patient operable instrumentation that, with upgrades as described herein, may be used according to the present invention.

Examples of Patient Operable Instrumentation:

FIG. 8 shows an example of one type of patient operable instrumentation that may be used according to the present invention. This type of device is discussed in more detail in copending application Ser. No. 14/186,151 and its provisional application 61/767,839; the entire contents of both of which are incorporated by reference in their entirety.

FIG. 9 shows an example of a different type of patient operable instrumentation that may be used according to the present invention. In this embodiment, the patient operable instrumentation is intended to be worn by the patient over a period of time. This type of device is discussed in more detail in provisional patent application 62/138,377, the entire contents of which are incorporated herein by reference. This device (900) can comprise an optional ear attachment device (902) that may have any of a temperature sensor and a pulse oximeter sensor. The device can also comprise a neck mounted device (904) that may contain an ECG sensor, batteries, and a computer processor. This neck mounted device may also comprise other types of sensors such as accelerometers, lung function sensors (e.g. microphones and audio processing circuitry to provide stethoscope like lung function assessment), and the like.

In some embodiments, other types of devices may also be attached to the neck mounted device. These other devices may include arm connectors (906) and armature wires that extend down to patient worn ECG electrodes (908), and the like.

User Medication Adherence Methods, and Machine Learning Methods:

In some embodiments, the invention may be configured to receive input from the user pertaining to which medications the user believes he or she has taken. Here, the invention may query the user regarding these medications (usually via a graphical user interface such as a touch sensitive display, or other methods such as audio queries and machine language recognition of audio responses).

For example, the invention may ask the user questions or surveys such as: "Did you take your medication [here the system may also provide an optional list of medications] on time today?" and give appropriate statistical weight to the user's responses. Here, for example, a "no" answer or a "non-response" answer might make the system give higher weight to the possibility that the user (patient) is not properly adhering to his or her medication schedule. Other survey questions can include questions regarding the patient's recent health status such as questions pertaining to nausea, abdominal pain, feeling generally weak, shortness of breath, cough, recent colds or flu, and so on.

Similarly, the invention may also be configured to receive input relating to other indicia of user/patient cooperation with healthcare professional recommendations. For example, input pertaining if the patient is adhering to other parts of the user/patient's health care plan, such as taking vital sign readings, adhering to scheduled meetings/consultations, providing on-time answers to questionnaires, and the like can also provide further information as to that user/patient's likely adherence to their medication schedule, or medication effectiveness if the patient is, in fact, adhering to the medication schedule.

Thus, for example, in situations where the physiological readings as to medication adherence, such as in FIG. 7 steps (724 and 726) are unclear, evidence that the patient has indicia of not cooperating with other healthcare recommendations may be used to alter the significance levels at which medication non-adherence is reported as being a potential problem. Conversely, if the patient has indicia of cooperating with healthcare recommendations, then other problems, such as lack of medication effectiveness, possibly caused by unexpected physiology, adverse drug interactions, changes in the patient's underlying medical condition, etc. can be reported.

Additionally, user surveys or behavioral data with regards to other aspects of healthcare compliance can also be used to extend the utility of the invention for a broader range of medications. This user survey or behavioral data may, for example, be particularly useful for patents (e.g., psychiatric patients) that may also be on medication that may not produce obvious changes in pulse wave data, for example.

Additionally, in some embodiments, various types of machine learning methods may also be used to enhance the utility of the invention. Examples of such machine learning methods include supervised learning approaches, such as the k-nearest neighbors algorithm (KNN) (see N. S. Altman, "*An Introduction to Kernel and Nearest-Neighbor Nonparametric Regression*", The American Statistician 46(3), 1992, pages 175-185). Other machine learning methods, such as artificial neural networks (ANNs) methods (Ganesan et. al., "*Application of Neural Networks in Diagnosing Cancer Disease Using Demographic Data*", International Journal of Computer Applications (0975-8887) Volume 1—No. 26, 2010); use of support vector machines or support vector networks (SVMs), (Cortes and Vapnick, "*Support-vector networks*", Machine Learning September 1995, Volume 20, Issue 3, pp 273-297) and the like may also be used.

These machine learning models may be pre-trained using data from investigational studies. Alternatively, or additionally, the input for these supervised machine learning techniques can be obtained from various combinations of the patient or user input, including healthcare professional input, and/or from the patient caretaker input as well.

Other types of machine learning methods, including unsupervised and reinforcement type machine learning, may also be used.

In some embodiments, these machine learning models will also employ features that could include any combination of the inputs gathered within the invention, such as the various physiological signals (or derived metrics), patient alarms, medication scheduling, patient demographic information, and the like.

The machine learning models (or indeed the invention in general) may, in turn, provide various types of output pertaining to patient medication adherence. In some embodiments, the output may be represented as a binary output (e.g., an automated "yes"/"no" assessment as to medication adherence, or medication effectiveness).

In other embodiments, the learning models (or again, the invention in general) may provide multi-value outputs pertaining to patient medication adherence and effectiveness. For example, the patient may be scored on a non-binary scale (such as very compliant, moderately compliant, and non-compliant). In other embodiments, the learning models (or again, the invention in general) may provide numerical scores as to likely patient compliance (e.g., a 0.0-10.0 score, such as 9.8 out of 10.0). At least to the extent that the patient is compliant, then other unexpected results can be attributed to lack of medication effectiveness. Other compliance and effectiveness output ratings, such as graphical or calendar data that show likely periods of compliance and non-compliance, or periods of medication effectiveness and the like may also be provided. In general, any graphical, alpha-numeric, sound or even tactile output pertaining to patient medication compliance or medication effectiveness may be provided by the invention.

As previously discussed, non-cuff type methods of obtaining blood pressure and blood pressure related pulse wave data include Photoplethysmography (PPG), Ballistocardiography, Phonocardiography, Advanced-Electrocardiography, Video Analysis, and high resolution (GHz+frequency) Radar. Here these methods are discussed in more detail below.

Photoplethysmography (PPG)

The volumetric change in blood flow measured through optical sensors is referred to as Photoplethysmography (PPG). PPG channels are often measured at 660 nm (red), 940 nm (infrared), and 525 nm (green) wavelengths. PPG sensors are either reflective (commonly placed on the forehead and wrist locations), or transmittance-based (commonly placed on the fingers, toes, ear lobes, and nasal cavity).

As PPG detects the changes in blood volume, it captures the pulse waveform, and as such provides information about the pulse rate, pulse rate variability, and the pulse morphology. The PPG waveform is commonly used in conjunction with the ECG waveform in order to estimate the pulse transit time (PTT), which can be used to accurately estimate blood pressure. However, the PPG waveform can also be used to estimate blood pressure without the use of other biosignals. This has been demonstrated using both pulse wave velocity (PWV) and pulse wave analysis (PWA) techniques.

Some examples of PWV-based techniques include
Estimation BP based on PTT determined using multiple PPG sensors
Estimation BP based on PTT determined using PPG combined with height and weight measurements
Some examples of PWA-based techniques include:
Estimation of BP using PPG-based machine learning methods
Estimation of BP using PPG-based multi-linear regression Ballistocardiography The Ballistocardiography (BCG) waveform measures vibrations that are produced by the body during the cardiac cycle. The ejection of blood during a cardiac cycle causes a reaction of the body associated with small variations in displacement, velocity, and acceleration. As such, there are various sensors that can be employed to measure the BCG, but these typically consist of some combination of an accelerometer (measurement of force/acceleration), magnetometer (measurement of a magnetic field), and/or gyroscope (measurement of angular rate). These form the basis of an inertial measurement unit. For example, piezoelectric films on chairs and beds, and force plates that measure recoil on a standing scale. Compared to most other methods, BCG measurement can be performed with minimal contact (no skin contact required) and is suitable for very long-term use.

Analysis of the BCG can be used to determine heart rate and heart rate variability, as well as other cardiovascular parameters. Furthermore, the BCG has been shown to have potential applications in cuffless blood pressure estimation and blood pressure estimation in combination with the PPG.

Phonocardiography (PCG)

The phonocardiography (PCG) waveform represents heart sounds associated with the opening and closing of the heart valves during the cardiac cycle. The PCG waveform can be acquired using a digital stethoscope in order to acquire a high fidelity recording of the four main heart sounds (S1, S2, S3, S4) that occur during each heartbeat.

Analysis of the PCG can be used to determine heart rate and heart rate variability. The PCG can also be used for detection and classification of heart murmurs and congenital heart disorders, such as ventricular and atrial septal defects. Furthermore, the PCG has been shown to be useful for cuffless blood pressure estimation when used in combination with the PPG to determine the vascular transit time, which is similar in concept to the more commonly used pulse transit time.

Electrocardiography

Advanced Electrocardiography (Advanced-ECG) measures the voltage associated with depolarization and repolarization during a cardiac cycle. The biopotentials, or currents in the body, are measured through electrodes, which are conductive pads attached to the skin. Disposable wet electrodes typically use Ag—AgCl contacts with electrolyte gel for conduction and dry electrodes use metal plating. A pair of electrodes measure the voltage potential difference between two points on the body. Heart rate and heart rate variability derivations can be determined by identifying R peaks within QRS complexes in ECG signals and calculating the average and standard deviation as measured by beats per minute. ECG is a clinical reference for diagnosing cardiac arrhythmias (such as Atrial Fibrillation), Myocardial Infarction, and coronary artery disease.

Advanced ECG methods leverage fundamental principles of biomechanics, as modelled through the Moens-Korteweg equations, pulse wave velocity (PWV) can be mapped to characteristics of the neighboring arterial wall. With an initial blood pressure calibration step, these equations can then be manipulated to derive Systolic and Diastolic estimates from pulse transit time as measured between ECG and photoplethysmography (PPG) peak-to-peak calculations.

Video Analysis

Recent advances have been made in the arena of non-contact, cuffless BP estimations from video recordings. PPG signals have been extracted from facial video recordings by enhancing the differential from frame-to-frame on the green and/or red channels for pulse rate or respiratory rate estimations. Blood pressure estimates are made from PTT by capturing video simultaneously of the face and hand. BP and HR have also been estimated directly from PPG signals extracted from facial recording through the analysis of time and frequency domain characteristics.

Radar Methods

Electromagnetic radar has demonstrated potential for non-invasive and remote sensing of vital sign measurements. A frequency modulated continuous wave (FMCW) radar operating at 77 GHz can detect chest wall movement, which is translated into heart rate and breathing rate estimates [1][2]. Radar technologies have also shown promise for remote glucose monitoring [3].

Examples of this type of work includes the work of Alizadeh and Shaker et. al., who investigated use of frequency modulated continuous wave (FMCW) radar operating at 77 GHz to determine heart rates and breathing rates. See Alizadeh et. al, IEEE access VOLUME 7, 2019, pages 54958 to 54968.

Trademarks: Corlanor® is a registered trademark of BIOFARMA société par actions simplifiée, Entresto® is a trademark of Novartis AG CORPORATION SWITZERLAND, Contrave® is a trademark of Orexigen Therapeutics, Inc. Narcan is a trademark of ENDO LABORATORIES INC. and ADAPT PHARMA OPERATIONS LIMITED.

The invention claimed is:

1. A method for determining a real-world effectiveness of at least one specific medication from a medication regimen comprising a plurality of medications, said method comprising:
obtaining patient operable instrumentation comprising a plurality of physiological monitoring devices configured to obtain a plurality of different types of actual patient pulse wave measurements comprising electrode-based time varying electrocardiograph (ECG) readings, and time varying blood oxygen saturation levels, and time varying blood pressure measurements;
said patient operable instrumentation further comprising at least one processor and memory;
wherein said patient operable instrumentation and said physiological monitoring devices are a unitized, common processor controlled, system;
obtaining a plurality of individual medication impact parameters, each individual medication impact parameter providing information on how an individual known specific medication alters a specific type of pulse wave measurements;
obtaining a plurality of patient reference information, each individual patient reference information providing information on a specific type of patient baseline pulse wave measurement in an absence of patient medication;
wherein said plurality of medication impact parameters and plurality of patient reference information further provide information on how they alter at least some of said plurality of different types of actual patient pulse wave measurements;
obtaining patient medication schedule information regarding said plurality of medications and medication dosing schedules for said patient, and storing said patient medication schedule in said memory;
obtaining and analyzing, using said at least one processor, a plurality of different types of actual patient pulse wave measurements at a known time;
calculating, using said at least one processor, expected patient pulse wave measurements based on said patient medication schedule information and said known time and said plurality of patient reference information and said plurality of medication impact parameters;
determining, using said at least one processor, which of said plurality of different types of actual patient pulse wave measurements are inconsistent with said expected patient pulse wave measurements, thus producing specific medications with inconsistent findings,
and using said processor to store at least said specific medications with inconsistent findings in said memory.

2. The method of claim 1, further obtaining patient alarm information, said patient alarm information reporting on any of blood oxygen saturation, blood pressure measurements, or electrocardiograph readings that fall outside of previously established boundaries; and
using said patient alarm information and those specific medications where inconsistent findings were obtained to determine and report that said patient is at risk of being ineffectively treated by those specific medications.

3. The method of claim 1, further using said processor to determine when inconsistent findings were obtained over more than one different type of actual patient pulse wave measurements; and
using said processor to determine that at least two different types of actual patient pulse wave measurements have inconsistent findings, and determining and reporting that said patient is at risk of being ineffectively treated by one or more specific medications.

4. The method of claim 1, wherein said plurality of medication impact parameters is determined by said processor by from at least one of either:
a) averages over a plurality of other patients in a presence and absence of said specific medication, further computing difference parameters between said presence and absence of said specific medication;
b) data obtained from said patient in said presence and absence of said specific medication, further computing difference parameters between said presence and absence of said specific medication.

5. The method of claim 1, wherein said plurality of patient reference information is determined by said processor from at least one of either:
a) averages over a plurality of other patients in an absence of said specific medication;
b) data obtained from said patient in said absence of said specific medication.

6. The method of claim 1, wherein said expected patient pulse wave measurements are determined by said processor from said patient medication schedule information and said known time and said plurality of patient reference information and said plurality of medication impact parameters by using said processor to transform said plurality of patient reference information into said expected patient pulse wave measurements by the steps of:
for each individual medication in said patient medication schedule information:
a) using selected corresponding individual medication impact parameters from said plurality of medication impact parameters to produce selected individual medication impact parameters;
b) applying, either analytically or empirically, said selected individual medication impact parameters to said plurality of patient reference information to produce intermediate transformed patient reference information;
c) producing said expected patient pulse wave measurements by repeating steps a and b until all individual medication in said patient medication schedule information has been processed.

7. The method of claim 1, wherein said patient operable instrumentation is further configured to receive compliance information from said patient reporting on periods of at least one of patient medication compliance or non-compliance, and to use said compliance information to select at least some actual patient pulse wave measurements for use in establishing or refining at least some of said medication impact parameters or said patient reference information.

8. The method of claim 1, further reporting at least some of those medications where inconsistent findings were determined by said processor to a remote computerized device over a network; and storing least some of those medication where inconsistent findings were obtained in at least one remote network computer memory.

9. The method of claim 1 wherein any of said plurality of medication impact parameters, plurality of patient reference information, and patient medication schedule information is either uploaded or downloaded by said processor over a network from a remote computerized device.

10. The method of claim 1, wherein said electrode-based time varying electrocardiograph (ECG) readings, and time varying blood oxygen saturation levels, and time varying blood pressure measurements are all performed simultaneously.

11. The method of claim 1, wherein said electrode-based time varying electrocardiograph (ECG) readings and said time varying blood oxygen saturation levels are simultaneously obtained using a same external combination finger pulse oximeter/ECG electrode device; and said time varying blood pressure measurements are simultaneously obtained using a blood pressure monitoring device.

12. The method of claim 1, wherein said electrode-based time varying electrocardiograph (ECG) readings, and time varying blood oxygen saturation levels, and time varying blood pressure measurements are all performed simultaneously so as to obtain synchronized pulse wave, hemoglobin absorbance, and electrocardiogram pulse wave information of the same patient heart beats.

13. The method of claim 1, wherein said effectiveness comprises an impact of said at least one specific medication on said patient's actual patient pulse wave measurements as compared to calculated expected patient pulse wave measurements for said medication regimen.

14. A method for determining a real-world effectiveness of at least one specific medication from a medication regimen comprising a plurality of medications, said method comprising:

obtaining patient operable instrumentation comprising a plurality of physiological monitoring devices configured to obtain a plurality of different types of actual patient pulse wave measurements comprising electrode-based time varying electrocardiograph (ECG) readings, and time varying blood oxygen saturation levels, and time varying blood pressure measurements;

said patient operable instrumentation further comprising at least one processor and memory;

wherein said patient operable instrumentation and said physiological monitoring devices are a unitized, common processor controlled, system;

wherein said electrode-based time varying electrocardiograph (ECG) readings, and time varying blood oxygen saturation levels, and time varying blood pressure measurements are all performed simultaneously so as to obtain synchronized pulse wave, hemoglobin absorbance, and electrocardiogram pulse wave information of the same patient heart beats;

obtaining a plurality of individual medication impact parameters, each individual medication impact parameter providing information on how an individual known specific medication alters a specific type of pulse wave measurements;

obtaining a plurality of patient reference information, each individual patient reference information providing information on a specific type of patient baseline pulse wave measurement in an absence of patient medication;

wherein said plurality of medication impact parameters and plurality of patient reference information further provide information on how they alter at least some of said plurality of different types of actual patient pulse wave measurements;

obtaining patient medication schedule information regarding said plurality of medications and medication dosing schedules for said patient, and storing said patient medication schedule in said memory;

obtaining and analyzing, using said at least one processor, a plurality of different types of actual patient pulse wave measurements at a known time;

calculating, using said at least one processor, expected patient pulse wave measurements based on said patient medication schedule information and said known time and said plurality of patient reference information and said plurality of medication impact parameters;

determining, using said at least one processor, which of said plurality of different types of actual patient pulse wave measurements are inconsistent with said expected patient pulse wave measurements, thus producing specific medications with inconsistent findings;

using said processor to store at least said specific medications with inconsistent findings in said memory; and further using said processor to determine when inconsistent findings were obtained over more than one different type of actual patient pulse wave measurements; and using said processor to determine that at least two different types of actual patient pulse wave measurements have inconsistent findings, and determining and reporting that said patient is at risk of being ineffectively treated by one or more specific medications.

15. A device for determining a real-world effectiveness of at least one specific medication from a medication regimen comprising a plurality of medications, said device comprising:

patient operable instrumentation comprising physiological monitoring devices configured to obtain a plurality of different types of actual patient pulse wave measurements comprising electrode-based time varying electrocardiograph (ECG) readings, and time varying blood oxygen saturation levels, and time varying blood pressure measurements types; said patient operable instrumentation further comprising at least one processor and memory;

wherein said patient operable instrumentation and said physiological monitoring devices are a unitized system, all managed by at least one common processor;

wherein said device is configured to obtain and store a plurality of individual medication impact parameters, each individual medication impact parameter providing information on how an individual known specific medication alters a specific type of pulse wave measurements;

wherein said plurality of medication impact parameters and plurality of patient reference information further provide information on how they alter at least some of said plurality of different types of actual patient pulse wave measurements;

wherein said device is further configured to obtain and store a plurality of patient reference information, each individual patient reference information providing information on a specific type of patient baseline pulse wave measurement in an absence of patient medication;

wherein said device is further configured to obtain and store patient medication schedule information regarding said at least one medication and medication dosing schedule for said patient;

said at least one processor further configured so that when said patient operable instrumentation is used on a patient with patient medication schedule information, said at least one processor is further configured to obtain a plurality of different types of actual pulse wave measurement at a known time, said at least one processor analyzes said plurality of different types of actual patient pulse wave measurements at a known time, and determines which of said plurality of different types of actual patient pulse wave measurements are inconsistent with those expected patient pulse wave measurements calculated from said patient medication schedule information, said known time, said plurality of patient reference information, and said plurality of medication impact parameters;

wherein said at least one processor is further configured to store at least those specific medications where inconsistent findings were obtained in said memory;

wherein said effectiveness comprises an impact of said at least one specific medication on a patient's actual patient pulse wave measurements as compared to calculated expected patient pulse wave measurements for said medication regimen.

16. The device of claim 15, wherein said at least one processor is further configured to provide patient alarm information, said patient alarm information reporting on when any of blood oxygen saturation, blood pressure measurements, or electrocardiograph readings fall outside of previously established boundaries; and wherein said device is configured to use said patient alarm information and those medications where inconsistent findings were obtained to determine and report that said patient may be ineffectively treated by those specific medications.

17. The device of claim 15, wherein said at least one processor is further configured to determine if inconsistent findings were obtained over more than one different type of actual patient pulse wave measurements; and wherein said device is configured so that when at least two different types of actual patient pulse wave measurements have inconsistent findings, said device further determines and reports that said patient may be ineffectively treated by those specific medications.

18. The device of claim 15, wherein said at least one processor is further configured to calculate said expected patient pulse wave measurements from said patient medication schedule information, said known time, said plurality of patient reference information, and said plurality of medication impact parameters by using said processor to transform said plurality of patient reference information into said expected patient pulse wave measurements by the steps of:

for each individual medication in said patient medication schedule information:
a) selecting corresponding individual medication impact parameters from said plurality of medication impact parameters, thus producing selected individual medication impact parameters;
b) applying, either analytically or empirically, said selected individual medication impact parameters to said plurality of patient reference information, thus producing intermediate transformed patient reference information;
c) repeating steps a and b until all individual medication in said patient medication schedule information has been processed, thus producing said expected patient pulse wave measurements.

19. The device of claim 15, wherein said patient operable instrumentation is further comprises means to receive compliance information from said patient reporting on periods of at least one of patient medication compliance or non-compliance; and wherein said at least one processor is further configured to use said compliance information to select at least some actual patient pulse wave measurements for use in establishing or refining at least some of said medication impact parameters or said patient reference information.

20. The device of claim 15, further configured with network interface means to allow said device to connect with at least one remote computerized device over a network;

wherein said at least one processor is further configured report at least some of those medications where inconsistent findings were obtained to said remote computerized device; and/or wherein said at least one processor is further configured to enable any of said plurality of medication impact parameters, plurality of patient reference information, and patient medication schedule information to be either uploaded or downloaded over a network from a remote computerized device.

21. The device of claim 15, further configured with at least one of a body temperature sensor and an accelerometer sensor, at least one lung function sensor, and a time varying electroencephalographic (EEG) reading sensor;

wherein said plurality of patient reference information further comprises at least one of baseline body temperature information, baseline patient motion data, baseline patient lung status data, or baseline patient EEG data;

wherein at least some of said medication impact parameters further provide information on how a specific medication alters at least one of said baseline body temperature information, said baseline patient motion data, baseline patient lung function, and said patient baseline EEG data;

wherein said at least one processor is further configured to use said patient medication schedule information, said known time, said plurality of patient reference information and at least some of said medication impact parameters to further determine if at least some specific medications are producing inconsistent findings.

22. The device of claim 15, wherein said device is configured to perform said electrode-based time varying electrocardiograph (ECG) readings, and time varying blood oxygen saturation levels, and time varying blood pressure measurements simultaneously so as to obtain synchronized pulse wave, hemoglobin absorbance, and electrocardiogram pulse wave information of the same patient heart beats.

* * * * *